(12) United States Patent
Denison

(10) Patent No.: US 7,452,542 B2
(45) Date of Patent: Nov. 18, 2008

(54) LIVE ATTENUATED CORONAVIRUS VACCINES

(75) Inventor: Mark Denison, Nashville, TN (US)

(73) Assignee: Vanderbilt University, Nashville, TN (US)

(*) Notice: Subject to any disclaimer, the term of this patent is extended or adjusted under 35 U.S.C. 154(b) by 275 days.

(21) Appl. No.: 11/135,603

(22) Filed: May 23, 2005

(65) Prior Publication Data

US 2006/0039926 A1 Feb. 23, 2006

Related U.S. Application Data

(60) Provisional application No. 60/573,587, filed on May 21, 2004.

(51) Int. Cl.
*A61K 39/215* (2006.01)
*C12N 7/00* (2006.01)
*C12N 7/04* (2006.01)
*C12N 15/50* (2006.01)

(52) U.S. Cl. ................ 424/221.1; 435/235.1; 435/236; 536/23.72

(58) Field of Classification Search ................ None
See application file for complete search history.

(56) References Cited

OTHER PUBLICATIONS

Enjuanes et al. Current Topics in Microbiology and Immunology 287: 161-197, 2005.*
Thiel et al. Current Topics in Microbiology and Immunology 287: 199-227, 2005.*
Masters et al. Current Topics in Microbiology and Immunology 287: 133-159. 2005.*
Gorbalenya et al. Virus Research 117:17-37, 2006.*
Cavanagh. Avian Pathology 32(6):567-582, 2003.*
Saif. "Animal Coronavirus Vaccines: Lessons for SARS." Developments in Biologicals 119:129-140, 2004.*
Index of Viruses—Coronaviridae (2006). In: ICTVdB—The Universal Virus Database, version 4. Büchen-Osmond, C (Ed), Columbia University, New York, USA. <<http://www.ncbi.nlm.nih.gov/ICTVdb/Ictv/fs_index.htm>> Downloaded Aug. 1, 2008.*
Baker et al., "Identification of the catalytic sites of a papain-like cysteine proteinase of murine coronavirus," *J. Virol.*, 67:6056-6063, 1993.
Bonilla et al., "Characterization of a second cleavage site and demonstration of activity in trans by the papain-like proteinase of the murine coronavirus mouse hepatitis virus strain A59," *J. Virol.*, 71:900-909, 1997.
Bonilla et al., "Characterization of the Leader Papain-like Proteinase of MHV-A59: Identification of a New in Vitro Cleavage Site," *Virology*, 209:489-497, 1995.
Boursnell et al., "Completion of the sequence of the genome of the coronavirus avian infectious bronchitis virus," *J. Gen. Virol.*, 68:57-77, 1987.
Chouljenko et al., "Comparison of genomic and predicted amino acid sequences of respiratory and enteric bovine coronaviruses isolated from the same animal with fatal shipping pneumonia," *J. Gen. Virol.*, 82:2927-2933, 2001.
Curtis et al., "Heterologous gene expression from transmissible gastroenteritis virus replicon particles," *J. Virol.*, 76:1422-1434, 2002.
Dong and Baker, "Determinants of the p28 Cleavage Site Recognized by the First Papain-like Cysteine Proteinase of Murin Coronavirus," *Virology*, 204:541-549, 1994.
Eleouet et al., "Complete Sequence (20 Kilobases) of the Polyprotein-Encoding Gene 1 of Transmissible Gastroenteritis Virus," *Virology*, 206:817-822, 1995.
Yoo and Pei, "Full-length genomic sequence of bovine coronavirus (31 kb). Completion of the open reading frame 1a/1b sequences," *Adv. Exp. Med. Biol.*, 494:73-76, 2001.
Yount et al., "Strategy for systematic assembly of large RNA and DNA genomes: transmissible gastroenteritis virus model," *J. Virol.*, 74:10600-10611, 2000.
Yount et al., "Systematic assembly of a full-length infectious cDNA of mouse hepatitis virus strain A59," *J. Virol.*, 76:11065-11078, 2002.
Ziebuhr et al., "The autocatalytic release of a putative RNA virus transcription factor from its polyprotein precursor involves two paralogous papain-like proteases that cleave the same peptide bond," *J. Biol. Chem.*, 276:33220-33232, 2001.
Genbank Accession No. AY274119, (2004).
Genbank Accession No. AY278491, (2003).
Genbank Accession No. AY278554, (2003).
Genbank Accession No. NC_001451, (2005).
Genbank Accession No. NC_001846, (2006).
Genbank Accession No. NC_002306, (2006).
Genbank Accession No. NC_002645, (2004).
Genbank Accession No. NC_003045, (2005).
Herold et al., "A human RNA viral cysteine proteinase that depends upon a unique Zn2+-binding finger connecting the two domains of a papain-like fold," *J. Biol. Chem.*, 274:14918-14925, 1999.
Herold et al., "Nucleotide Sequence of the Human Coronavirus 229E RNA Polymerase Locus," *Virology*, 195:680-691, 1993.
Hughes et al., "Identification of the murine coronavirus p. 28 cleavage site," *J. Virol.*, 69:809-813, 1995.
Kanjanahaluethai and Baker, "Identification of mouse hepatitis virus papain-like proteinase 2 activity," *J. Virol.*, 74:7911-7921, 2000.
Kanjanahaluethai and Baker., "Processing of the replicase of murine coronavirus: papain-like proteinase 2 (PLP2) acts to generate p. 150 and p. 44," *Adv. Exp. Med. Biol.*, 494:267-273, 2001.
Lee et al., "The Complete Sequence (22 Kilobases) of Murine Coronavirus Gene 1 Encoding the Putative Proteases and RNA Polymerase," *Virology*, 180:567-582, 1991.
Schaad et al., "Genetics of Mouse Hepatitis Virus Transcription: Identification of Cistrons which May Function in Positive and Negative Strand RNA Synthesis," *Virology*, 177:634-645, 1990.
Tijms et al., "A zinc finger-containing papain-like protease couples subgenomic mRNA synthesis to genome translation in a positive-stranded RNA virus," *Proc. Natl. Acad. Sci. USA*, 98:1889-1894, 2001.

* cited by examiner

*Primary Examiner*—Mary E Mosher
(74) *Attorney, Agent, or Firm*—Fulbright & Jaworski

(57) ABSTRACT

The present invention is directed live, attenuated coronavirus vaccines. The vaccine comprises a viral genome encoding a p59 protein having at mutation at a specific tyrosine residue, and may include other attenuating mutations. Such viruses show reduced growth and pathogenicity in vivo.

32 Claims, 5 Drawing Sheets

| Virus | Amino Acids | LD$_{50}$ (PFU) | LD$_{50}$ Log$_{10}$ |
|---|---|---|---|
| RA59 | wtA59 Tyr$_{6398}$Leu$_{106}$ | 6.32*10$^3$ | 3.8 |
| icwt (uncorrected) | His$_{6398}$Pro$_{106}$ | >2*10$^5$ | >5.3 |
| VUSS-1 | Tyr$_{6398}$Pro$_{106}$ | 4.74*10$^4$ | 4.67 |
| VUSS-2 | His$_{6398}$Leu$_{106}$ | >2*10$^5$ | >5.3 |
| VUSS-3 | Tyr$_{6398}$Leu$_{106}$ | 6.32*10$^3$ | 3.8 |

FIG. 3A-B

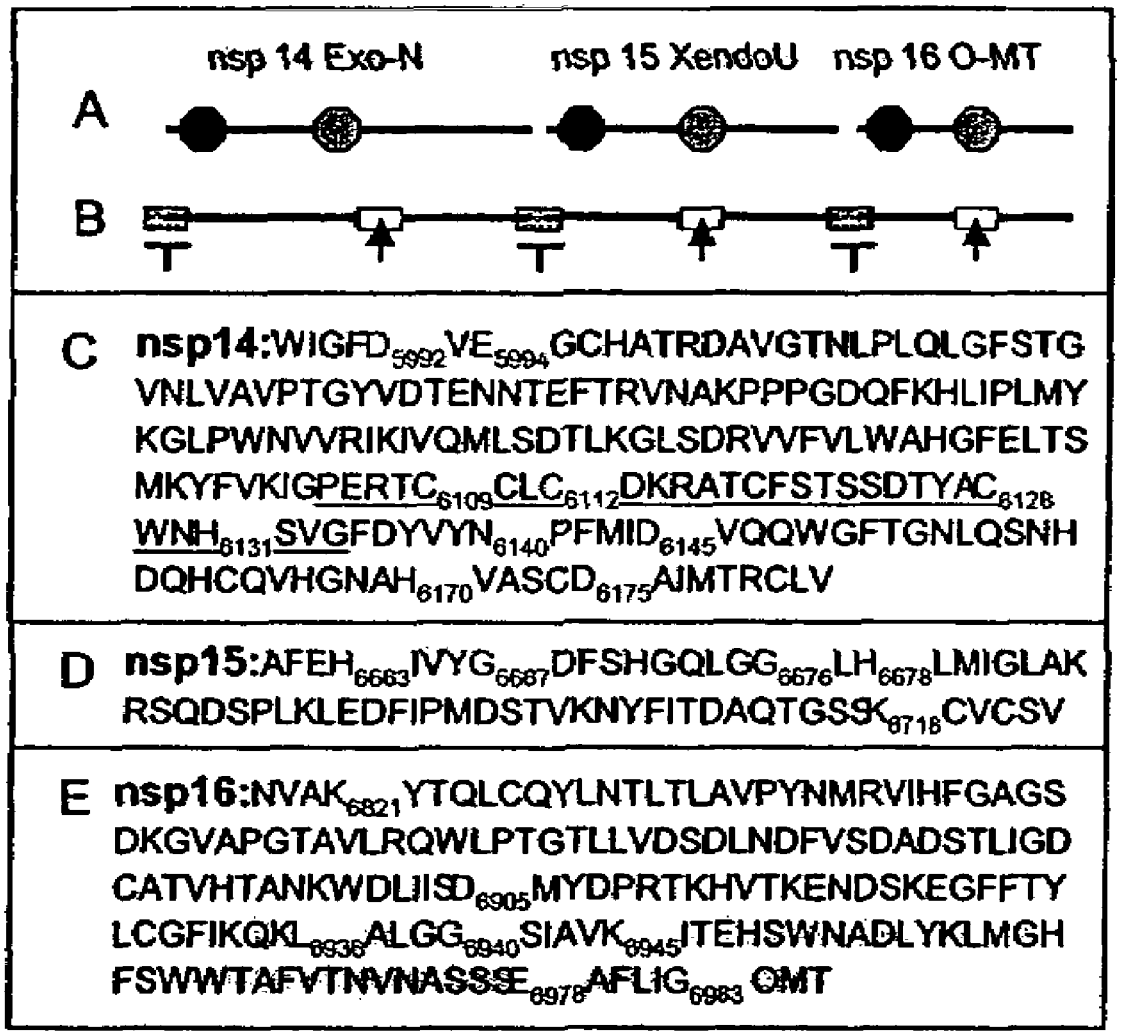
FIG. 5A-E

SEQUENCE LISTING

```
<160> NUMBER OF SEQ ID NOS: 12

<210> SEQ ID NO 1
<211> LENGTH: 521
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1

Cys Thr Thr Asn Leu Phe Lys Asp Cys Ser Arg Ser Tyr Val Gly Tyr
 1               5                  10                  15

His Pro Ala His Ala Pro Ser Phe Leu Ala Val Asp Asp Lys Tyr Lys
            20                  25                  30

Val Gly Gly Asp Leu Ala Val Cys Leu Asn Val Ala Asp Ser Ala Val
        35                  40                  45

Thr Tyr Ser Arg Leu Ile Ser Leu Met Gly Phe Lys Leu Asp Leu Thr
    50                  55                  60

Leu Asp Gly Tyr Cys Lys Leu Phe Ile Thr Arg Asp Glu Ala Ile Lys
65                  70                  75                  80

Arg Val Arg Ala Trp Val Gly Phe Asp Ala Glu Gly Ala His Ala Ile
                85                  90                  95

Arg Asp Ser Ile Gly Thr Asn Phe Pro Leu Gln Leu Gly Phe Ser Thr
            100                 105                 110

Gly Ile Asp Phe Val Val Glu Ala Thr Gly Met Phe Ala Glu Arg Asp
```

```
                115                 120                 125
Gly Tyr Val Phe Lys Lys Ala Ala Arg Ala Pro Gly Glu Gln
    130                 135                 140
Gly Lys His Leu Ile Pro Leu Met Ser Arg Gly Gln Lys Trp Asp Val
145                 150                 155                 160
Val Arg Ile Arg Ile Val Gln Met Leu Ser Asp His Leu Ala Asp Leu
                165                 170                 175
Ala Asp Ser Val Val Leu Val Thr Trp Ala Ala Ser Phe Glu Leu Thr
            180                 185                 190
Cys Leu Arg Tyr Phe Ala Lys Val Gly Arg Glu Val Val Cys Ser Val
            195                 200                 205
Cys Thr Lys Arg Ala Thr Cys Phe Asn Ser Arg Thr Gly Tyr Tyr Gly
    210                 215                 220
Cys Trp Arg His Ser Tyr Ser Cys Asp Tyr Leu Tyr Asn Pro Leu Ile
225                 230                 235                 240
Val Asp Ile Gln Gln Trp Gly Tyr Thr Gly Ser Leu Thr Ser Asn His
                245                 250                 255
Asp Pro Ile Cys Ser Val His Lys Gly Ala His Val Ala Ser Ser Asp
                260                 265                 270
Ala Ile Met Thr Arg Cys Leu Ala Val His Asp Cys Phe Cys Lys Ser
            275                 280                 285
Val His Trp Asn Leu Glu Tyr Pro Ile Ile Ser Asn Glu Val Ser Val
    290                 295                 300
Asn Thr Ser Cys Arg Leu Leu Gln Arg Val Met Phe Arg Ala Ala Met
305                 310                 315                 320
Leu Cys Asn Arg Tyr Asp Val Cys Tyr Asp Ile Gly Asn Pro Lys Gly
                325                 330                 335
Leu Ala Cys Val Lys Gly Tyr Asp Phe Lys Phe Tyr Asp Ala Ser Pro
            340                 345                 350
Val Val Lys Ser Val Lys Gln Phe Val Tyr Lys Tyr Glu Ala Asn Lys
            355                 360                 365
Asp Gln Phe Leu Asp Gly Leu Cys Met Phe Trp Asn Cys Asn Val Asp
    370                 375                 380
Lys Tyr Pro Ala Asn Ala Val Val Cys Arg Phe Asp Thr Arg Val Leu
385                 390                 395                 400
Asn Lys Leu Asn Leu Pro Gly Cys Asn Gly Gly Ser Leu Tyr Val Asn
                405                 410                 415
Lys His Ala Phe His Thr Ser Pro Phe Thr Arg Ala Ala Phe Glu Asn
                420                 425                 430
Leu Lys Pro Met Pro Phe Phe Tyr Tyr Ser Asp Thr Pro Cys Val Tyr
            435                 440                 445
Met Glu Gly Met Glu Ser Lys Gln Val Asp Tyr Val Pro Leu Arg Ser
    450                 455                 460
Ala Thr Cys Ile Thr Arg Cys Asn Leu Gly Gly Ala Val Cys Leu Lys
465                 470                 475                 480
His Ala Glu Glu Tyr Arg Glu Tyr Leu Glu Ser Tyr Asn Thr Ala Thr
                485                 490                 495
Thr Ala Gly Phe Thr Phe Trp Val Tyr Lys Thr Phe Asp Phe Tyr Asn
            500                 505                 510
Leu Trp Asn Thr Phe Thr Arg Leu Gln
            515                 520

<210> SEQ ID NO 2
```

<211> LENGTH: 527
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 2

```
Ala Glu Asn Val Thr Gly Leu Phe Lys Asp Cys Ser Lys Ile Ile Thr
 1               5                  10                  15

Gly Leu His Pro Thr Gln Ala Pro Thr His Leu Ser Val Asp Ile Lys
            20                  25                  30

Phe Lys Thr Glu Gly Leu Cys Val Asp Ile Pro Gly Ile Pro Lys Asp
        35                  40                  45

Met Thr Tyr Arg Arg Leu Ile Ser Met Met Gly Phe Lys Met Asn Tyr
    50                  55                  60

Gln Val Asn Gly Tyr Pro Asn Lys Phe Ile Thr Arg Glu Glu Ala Ile
65                  70                  75                  80

Arg His Val Arg Ala Trp Ile Gly Phe Asp Val Glu Gly Cys His Ala
                85                  90                  95

Thr Arg Asp Ala Val Gly Thr Asn Leu Pro Leu Gln Leu Gly Phe Ser
            100                 105                 110

Thr Gly Val Asn Leu Val Ala Val Pro Thr Gly Tyr Val Asp Thr Glu
        115                 120                 125

Asn Asn Thr Glu Phe Thr Arg Val Asn Ala Lys Pro Pro Pro Gly Asp
    130                 135                 140

Gln Phe Lys His Leu Ile Pro Leu Met Tyr Lys Gly Leu Pro Trp Asn
145                 150                 155                 160

Val Val Arg Ile Lys Ile Val Gln Met Leu Ser Asp Thr Leu Lys Gly
                165                 170                 175

Leu Ser Asp Arg Val Val Phe Val Leu Trp Ala His Gly Phe Glu Leu
            180                 185                 190

Thr Ser Met Lys Tyr Phe Val Lys Ile Gly Pro Glu Arg Thr Cys Cys
        195                 200                 205

Leu Cys Asp Lys Arg Ala Thr Cys Phe Ser Thr Ser Ser Asp Thr Tyr
    210                 215                 220

Ala Cys Trp Asn His Ser Val Gly Phe Asp Tyr Val Tyr Asn Pro Phe
225                 230                 235                 240

Met Ile Asp Val Gln Gln Trp Gly Phe Thr Gly Asn Leu Gln Ser Asn
                245                 250                 255

His Asp Gln His Cys Gln Val His Gly Asn Ala His Val Ala Ser Cys
            260                 265                 270

Asp Ala Ile Met Thr Arg Cys Leu Ala Val His Glu Cys Phe Val Lys
        275                 280                 285

Arg Val Asp Trp Ser Val Glu Tyr Pro Ile Ile Gly Asp Glu Leu Arg
    290                 295                 300

Val Asn Ser Ala Cys Arg Lys Val Gln His Met Val Val Lys Ser Ala
305                 310                 315                 320

Leu Leu Ala Asp Lys Phe Pro Val Leu His Asp Ile Gly Asn Pro Lys
                325                 330                 335

Ala Ile Lys Cys Val Pro Gln Ala Glu Val Glu Trp Lys Phe Tyr Asp
            340                 345                 350

Ala Gln Pro Cys Ser Asp Lys Ala Tyr Lys Ile Glu Glu Leu Phe Tyr
        355                 360                 365

Ser Tyr Ala Thr His His Asp Lys Phe Thr Asp Gly Val Cys Leu Phe
```

```
              370                 375                 380
Trp Asn Cys Asn Val Asp Arg Tyr Pro Ala Asn Ala Ile Val Cys Arg
385                 390                 395                 400

Phe Asp Thr Arg Val Leu Ser Asn Leu Asn Leu Pro Gly Cys Asp Gly
                405                 410                 415

Gln Ser Leu Tyr Val Asn Lys His Ala Phe His Thr Pro Ala Phe Asp
                420                 425                 430

Lys Ser Ala Phe Thr Asn Leu Lys Gln Leu Pro Phe Phe Tyr Tyr Ser
                435                 440                 445

Asp Ser Pro Cys Glu Ser His Gly Lys Gln Val Val Ser Asp Ile Asp
450                 455                 460

Tyr Val Pro Leu Lys Ser Ala Thr Cys Ile Thr Arg Cys Asn Leu Gly
465                 470                 475                 480

Gly Ala Val Cys Arg His His Ala Asn Glu Tyr Arg Gln Tyr Leu Asp
                485                 490                 495

Ala Tyr Asn Met Met Ile Ser Ala Gly Phe Ser Leu Trp Ile Tyr Lys
                500                 505                 510

Gln Phe Asp Thr Tyr Asn Leu Trp Asn Thr Phe Thr Arg Leu Gln
                515                 520                 525

<210> SEQ ID NO 3
<211> LENGTH: 521
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 3

Cys Ser Thr Asn Leu Phe Lys Asp Cys Ser Lys Ser Tyr Ser Gly Tyr
1               5                   10                  15

His Pro Ala His Ala Pro Ser Phe Leu Ala Val Asp Asp Lys Tyr Lys
                20                  25                  30

Ala Thr Gly Asp Leu Ala Val Cys Leu Gly Ile Gly Asp Ser Ala Val
            35                  40                  45

Thr Tyr Ser Arg Leu Ile Ser Leu Met Gly Phe Lys Leu Asp Val Thr
    50                  55                  60

Leu Asp Gly Tyr Cys Lys Leu Phe Ile Thr Lys Glu Glu Ala Val Lys
65                  70                  75                  80

Arg Val Arg Ala Trp Val Gly Phe Asp Ala Glu Gly Ala His Ala Thr
                85                  90                  95

Arg Asp Ser Ile Gly Thr Asn Phe Pro Leu Gln Leu Gly Phe Ser Thr
            100                 105                 110

Gly Ile Asp Phe Val Val Glu Ala Thr Gly Leu Phe Ala Asp Arg Asp
        115                 120                 125

Gly Tyr Ser Phe Lys Lys Ala Val Ala Lys Ala Pro Gly Glu Gln
    130                 135                 140

Phe Lys His Leu Ile Pro Leu Met Thr Arg Gly Gln Arg Trp Asp Val
145                 150                 155                 160

Val Arg Pro Arg Ile Val Gln Met Phe Ala Asp His Leu Ile Asp Leu
                165                 170                 175

Ser Asp Cys Val Val Leu Val Thr Trp Ala Ala Asn Phe Glu Leu Thr
            180                 185                 190

Cys Leu Arg Tyr Phe Ala Lys Val Gly Arg Glu Ile Ser Cys Asn Val
        195                 200                 205
```

```
Cys Thr Lys Arg Ala Thr Ala Tyr Asn Ser Arg Thr Gly Tyr Tyr Gly
    210                 215                 220

Cys Trp Arg His Ser Val Thr Cys Asp Tyr Leu Tyr Asn Pro Leu Ile
225                 230                 235                 240

Val Asp Ile Gln Gln Trp Gly Tyr Ile Gly Ser Leu Ser Ser Asn His
                245                 250                 255

Asp Leu Tyr Cys Ser Val His Lys Gly Ala His Val Ala Ser Ser Asp
            260                 265                 270

Ala Ile Met Thr Arg Cys Leu Ala Val Tyr Asp Cys Phe Cys Asn Asn
        275                 280                 285

Ile Asn Trp Asn Val Glu Tyr Pro Ile Ile Ser Asn Glu Leu Ser Ile
    290                 295                 300

Asn Thr Ser Cys Arg Val Leu Gln Arg Val Met Leu Lys Ala Ala Met
305                 310                 315                 320

Leu Cys Asn Arg Tyr Thr Leu Cys Tyr Asp Ile Gly Asn Pro Lys Ala
                325                 330                 335

Ile Ala Cys Val Lys Asp Phe Asp Phe Lys Phe Tyr Asp Ala Gln Pro
            340                 345                 350

Ile Val Lys Ser Val Lys Thr Leu Leu Tyr Ser Phe Glu Ala His Lys
        355                 360                 365

Asp Ser Phe Lys Asp Gly Leu Cys Met Phe Trp Asn Cys Asn Val Asp
    370                 375                 380

Lys Tyr Pro Pro Asn Ala Val Val Cys Arg Phe Asp Thr Arg Val Leu
385                 390                 395                 400

Asn Asn Leu Asn Leu Pro Gly Cys Asn Gly Gln Ser Leu Tyr Val Asn
                405                 410                 415

Lys His Ala Phe His Thr Lys Pro Phe Ser Arg Ala Ala Phe Glu His
            420                 425                 430

Leu Lys Pro Met Pro Phe Phe Tyr Tyr Ser Asp Thr Pro Cys Val Tyr
        435                 440                 445

Met Asp Gly Met Asp Ala Lys Gln Val Asp Tyr Val Pro Leu Lys Ser
    450                 455                 460

Ala Thr Cys Ile Thr Arg Cys Asn Leu Gly Gly Ala Val Cys Leu Lys
465                 470                 475                 480

His Ala Glu Glu Tyr Arg Glu Tyr Leu Glu Ser Tyr Asn Thr Ala Thr
                485                 490                 495

Thr Ala Gly Phe Thr Phe Trp Val Tyr Lys Thr Phe Asp Phe Tyr Asn
            500                 505                 510

Leu Trp Asn Thr Phe Thr Lys Leu Gln
        515                 520

<210> SEQ ID NO 4
<211> LENGTH: 521
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 4

Cys Ser Thr Asn Leu Phe Lys Asp Cys Ser Lys Ser Tyr Ser Gly Tyr
  1               5                  10                  15

His Pro Ala His Ala Pro Ser Phe Leu Ala Val Asp Asp Lys Tyr Lys
                20                  25                  30

Ala Thr Gly Asp Leu Ala Val Cys Leu Gly Ile Gly Asp Ser Ala Val
            35                  40                  45
```

-continued

```
Thr Tyr Ser Arg Leu Ile Ser Leu Met Gly Phe Lys Leu Asp Val Thr
     50                  55                  60

Leu Asp Gly Tyr Cys Lys Leu Phe Ile Thr Lys Glu Glu Ala Val Lys
 65                  70                  75                  80

Arg Val Arg Ala Trp Val Gly Phe Asp Ala Glu Gly Ala His Ala Thr
                     85                  90                  95

Arg Asp Ser Ile Gly Thr Asn Phe Pro Leu Gln Leu Gly Phe Ser Thr
                100                 105                 110

Gly Ile Asp Phe Val Val Glu Ala Thr Gly Leu Phe Ala Asp Arg Asp
                115                 120                 125

Gly Tyr Ser Phe Lys Lys Ala Val Ala Lys Ala Pro Pro Gly Glu Gln
            130                 135                 140

Phe Lys His Leu Ile Pro Leu Met Thr Arg Gly His Arg Trp Asp Val
145                 150                 155                 160

Val Arg Pro Arg Ile Val Gln Met Phe Ala Asp His Leu Ile Asp Leu
                165                 170                 175

Ser Asp Cys Val Val Leu Val Thr Trp Ala Ala Asn Phe Glu Leu Thr
                180                 185                 190

Cys Leu Arg Tyr Phe Ala Lys Val Gln Arg Glu Ile Ser Cys Asn Val
            195                 200                 205

Cys Thr Lys Arg Ala Thr Val Tyr Asn Ser Arg Thr Gly Tyr Tyr Gly
210                 215                 220

Cys Trp Arg His Ser Val Thr Cys Asp Tyr Leu Tyr Asn Pro Leu Ile
225                 230                 235                 240

Val Asp Ile Gln Gln Trp Gly Tyr Ile Gly Ser Leu Ser Ser Asn His
                245                 250                 255

Asp Leu Tyr Cys Ser Val His Lys Gly Ala His Val Ala Ser Ser Asp
                260                 265                 270

Ala Ile Met Thr Arg Cys Leu Ala Val Tyr Asp Cys Phe Cys Asn Asn
            275                 280                 285

Ile Asn Trp Asn Val Glu Tyr Pro Ile Ile Ser Asn Glu Leu Ser Ile
290                 295                 300

Asn Thr Ser Cys Arg Val Leu Gln Arg Val Ile Leu Lys Ala Ala Met
305                 310                 315                 320

Leu Cys Asn Arg Tyr Thr Leu Cys Tyr Asp Ile Gly Asn Pro Lys Ala
                325                 330                 335

Ile Ala Cys Val Lys Asp Phe Asp Phe Lys Phe Tyr Asp Ala Gln Pro
                340                 345                 350

Ile Val Lys Ser Val Lys Thr Leu Leu Tyr Ser Phe Glu Ala His Lys
            355                 360                 365

Asp Ser Phe Lys Asp Gly Leu Cys Met Phe Trp Asn Cys Asn Val Asp
    370                 375                 380

Lys Tyr Pro Pro Asn Ala Val Val Cys Arg Phe Asp Thr Arg Val Leu
385                 390                 395                 400

Asn Asn Leu Asn Leu Pro Gly Cys Asn Gly Gly Ser Leu Tyr Val Asn
                405                 410                 415

Lys His Ala Phe His Thr Lys Pro Phe Ala Arg Ala Ala Phe Glu His
                420                 425                 430

Leu Lys Pro Met Pro Phe Phe Tyr Tyr Ser Asp Thr Pro Cys Val Tyr
            435                 440                 445

Met Asp Gly Met Asp Ala Lys Gln Val Asp Tyr Val Pro Leu Lys Ser
450                 455                 460
```

```
Ala Thr Cys Ile Thr Lys Cys Asn Leu Gly Gly Ala Val Cys Leu Lys
465                 470                 475                 480

His Ala Glu Glu Tyr Arg Glu Tyr Leu Glu Ser Tyr Asn Thr Ala Thr
                485                 490                 495

Thr Ala Gly Phe Thr Phe Trp Val Tyr Lys Thr Phe Asp Phe Tyr Asn
            500                 505                 510

Leu Trp Asn Thr Phe Thr Lys Leu Gln
        515                 520

<210> SEQ ID NO 5
<211> LENGTH: 521
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 5

Gly Thr Gly Leu Phe Lys Ile Cys Asn Lys Glu Phe Ser Gly Val His
1               5                   10                  15

Pro Ala Tyr Ala Val Thr Thr Lys Ala Leu Ala Ala Thr Tyr Lys Val
            20                  25                  30

Asn Asp Glu Leu Ala Ala Leu Val Asn Val Glu Ala Gly Ser Glu Ile
        35                  40                  45

Thr Tyr Lys His Leu Ile Ser Leu Leu Gly Phe Lys Met Ser Val Asn
50                  55                  60

Val Glu Gly Cys His Asn Met Phe Ile Thr Arg Asp Glu Ala Ile Arg
65              70                  75                  80

Asn Val Arg Gly Trp Val Gly Phe Asp Val Glu Ala Thr His Ala Cys
            85                  90                  95

Gly Thr Asn Ile Gly Thr Asn Leu Pro Phe Gln Val Gly Phe Ser Thr
        100                 105                 110

Gly Ala Asp Phe Val Val Thr Pro Glu Gly Leu Val Asp Thr Ser Ile
    115                 120                 125

Gly Asn Asn Phe Glu Pro Val Asn Ser Lys Ala Pro Pro Gly Glu Gln
130                 135                 140

Phe Asn His Leu Arg Val Leu Phe Lys Ser Ala Lys Pro Trp His Val
145                 150                 155                 160

Ile Arg Pro Arg Ile Val Gln Met Leu Ala Asp Asn Leu Cys Asn Val
                165                 170                 175

Ser Asp Cys Val Val Phe Val Thr Trp Cys His Gly Leu Glu Leu Thr
            180                 185                 190

Thr Leu Arg Tyr Phe Val Lys Ile Gly Lys Glu Gln Val Cys Ser Cys
        195                 200                 205

Gly Ser Arg Ala Thr Thr Phe Asn Ser His Thr Gln Ala Tyr Ala Cys
    210                 215                 220

Trp Lys His Cys Leu Gly Phe Asp Phe Val Tyr Asn Pro Leu Leu Val
225                 230                 235                 240

Asp Ile Gln Gln Trp Gly Tyr Ser Gly Asn Leu Gln Phe Asn His Asp
                245                 250                 255

Leu His Cys Asn Val His Gly His Ala His Val Ala Ser Val Asp Ala
            260                 265                 270

Ile Met Thr Arg Cys Leu Ala Ile Asn Asn Ala Phe Cys Gln Asp Val
        275                 280                 285

Asn Trp Asp Leu Thr Tyr Phe His Ile Ala Asn Glu Asp Glu Val Asn
    290                 295                 300
```

```
Ser Ser Cys Arg Tyr Leu Gln Arg Met Tyr Leu Asn Ala Cys Val Asp
305                 310                 315                 320

Ala Leu Lys Val Asn Val Val Tyr Asp Ile Gly Asn Pro Lys Gly Ile
                325                 330                 335

Lys Cys Val Arg Arg Gly Asp Val Asn Phe Arg Phe Tyr Asp Lys Asn
            340                 345                 350

Pro Ile Val Arg Asn Val Lys Gln Phe Glu Tyr Asp Tyr Asn Gln His
        355                 360                 365

Lys Asp Lys Phe Ala Asp Gly Leu Cys Met Phe Trp Asn Cys Asn Val
    370                 375                 380

Asp Cys Tyr Pro Asp Asn Ser Leu Val Cys Arg Tyr Asp Thr Arg Asn
385                 390                 395                 400

Leu Ser Val Phe Asn Leu Pro Gly Cys Asn Gly Gly Ser Leu Tyr Val
                405                 410                 415

Asn Lys His Ala Phe Tyr Thr Pro Lys Phe Asp Arg Ile Ser Phe Arg
            420                 425                 430

Asn Leu Lys Ala Met Pro Phe Phe Tyr Asp Ser Ser Pro Cys Glu
        435                 440                 445

Thr Ile Gln Val Asp Gly Val Ala Gln Asp Leu Val Ser Leu Ala Thr
    450                 455                 460

Lys Asp Cys Ile Thr Lys Cys Asn Ile Gly Gly Ala Val Cys Lys Lys
465                 470                 475                 480

His Ala Gln Met Tyr Ala Glu Phe Val Thr Ser Tyr Asn Ala Ala Val
                485                 490                 495

Thr Ala Gly Phe Thr Phe Trp Val Thr Asn Lys Leu Asn Pro Tyr Asn
            500                 505                 510

Leu Trp Lys Ser Phe Ser Ala Leu Gln
        515                 520

<210> SEQ ID NO 6
<211> LENGTH: 519
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Ala Lys Pro Glu Thr Cys Gly Leu Phe Lys Asp Cys Ser Lys Ser Glu
1               5                   10                  15

Gln Tyr Ile Pro Pro Ala Tyr Ala Thr Thr Tyr Met Ser Leu Ser Asp
            20                  25                  30

Asn Phe Lys Thr Ser Asp Gly Leu Ala Val Asn Ile Gly Thr Lys Asp
        35                  40                  45

Val Lys Tyr Ala Asn Val Ile Ser Tyr Met Gly Phe Arg Phe Glu Ala
    50                  55                  60

Asn Ile Pro Gly Tyr His Thr Leu Phe Cys Thr Arg Asp Phe Ala Met
65                  70                  75                  80

Arg Asn Val Arg Ala Trp Leu Gly Phe Asp Val Glu Gly Ala Asn Val
                85                  90                  95

Cys Gly Asp Asn Val Gly Thr Asn Val Pro Leu Gly Leu Gly Phe Ser
            100                 105                 110

Asn Gly Val Asp Phe Val Val Gln Thr Glu Gly Cys Val Ile Thr Glu
        115                 120                 125

Lys Gly Asn Ser Ile Glu Val Val Lys Ala Arg Ala Pro Pro Gly Glu
```

```
            130                 135                 140
Gln Phe Ala His Leu Ile Pro Leu Met Arg Lys Gly Gln Pro Trp His
145                 150                 155                 160

Ile Val Arg Arg Ile Val Gln Met Val Cys Asp Tyr Phe Asp Gly
            165                 170                 175

Leu Ser Asp Ile Leu Ile Phe Val Leu Trp Ala Gly Gly Leu Glu Leu
                180                 185                 190

Thr Thr Met Arg Tyr Phe Val Lys Ile Gly Arg Pro Gln Lys Cys Glu
            195                 200                 205

Cys Gly Lys Ser Ala Thr Cys Tyr Ser Ser Gln Ser Val Tyr Ala
210                 215                 220

Cys Phe Lys His Ala Leu Gly Cys Asp Tyr Leu Tyr Asn Pro Tyr Cys
225                 230                 235                 240

Ile Asp Ile Gln Gln Trp Gly Tyr Thr Gly Ser Leu Ser Met Met His
                245                 250                 255

His Glu Val Cys Asn Ile His Arg Asn Glu His Val Ala Ser Gly Asp
            260                 265                 270

Ala Ile Met Thr Arg Cys Leu Ala Ile His Asp Cys Phe Val Lys Arg
            275                 280                 285

Val Asp Trp Ser Ile Val Tyr Pro Phe Ile Asp Asn Glu Glu Lys Ile
            290                 295                 300

Met Lys Ala Gly Arg Ile Val Gly Ser His Val Met Lys Ala Ala Leu
305                 310                 315                 320

Lys Ile Phe Asn Pro Ala Ala Ile Asn Asp Val Gly Asn Pro Lys Gly
                325                 330                 335

Ile Arg Cys Ala Thr Thr Pro Ile Pro Trp Phe Cys Tyr Asp Arg Asp
            340                 345                 350

Pro Ile Asn Asn Asn Val Arg Cys Leu Asp Tyr Asp Tyr Met Val Met
            355                 360                 365

Gly Gln Met Asn Gly Leu Met Leu Phe Trp Asn Cys Asn Val Asp Met
            370                 375                 380

Tyr Pro Glu Phe Ser Ile Val Cys Arg Phe Asp Thr Arg Thr Arg Ser
385                 390                 395                 400

Lys Leu Ser Leu Glu Gly Cys Asn Gly Gly Ala Leu Tyr Val Asn Asn
                405                 410                 415

His Ala Phe Met Thr Pro Ala Tyr Asp Arg Arg Ala Phe Ala Lys Leu
            420                 425                 430

Lys Pro Met Pro Phe Phe Tyr Tyr Asp Asp Ser Asn Cys Glu Leu Val
            435                 440                 445

Asp Gly Gln Pro Asn Tyr Val Pro Leu Lys Ser Asn Val Cys Ile Thr
450                 455                 460

Lys Cys Asn Ile Gly Gly Ala Val Cys Lys Lys His Ala Ala Leu Tyr
465                 470                 475                 480

Arg Ala Tyr Val Glu Asp Tyr Asn Ile Phe Met Gln Ala Gly Phe Thr
                485                 490                 495

Ile Trp Cys Pro Gln Asn Phe Asp Thr Tyr Met Leu Trp His Gly Phe
            500                 505                 510

Val Asn Ser Lys Ala Leu Gln
        515

<210> SEQ ID NO 7
<211> LENGTH: 518
<212> TYPE: PRT
<213> ORGANISM: Artificial Sequence
```

```
<220> FEATURE:
<223> OTHER INFORMATION: Description of Artificial Sequence:  Synthetic
      Peptide

<400> SEQUENCE: 7

Ser Glu Ser Ser Cys Gly Leu Phe Lys Asp Cys Ala Arg Asn Pro Ile
1               5                   10                  15

Asp Leu Pro Pro Ser His Ala Thr Thr Tyr Leu Ser Leu Ser Asp Arg
            20                  25                  30

Phe Lys Thr Ser Gly Asp Leu Ala Val Gln Ile Gly Asn Asn Asn Val
        35                  40                  45

Cys Thr Tyr Glu His Val Ile Ser Tyr Met Gly Phe Arg Phe Asp Val
    50                  55                  60

Ser Met Pro Gly Ser His Ser Leu Phe Cys Thr Arg Asp Phe Ala Met
65                  70                  75                  80

Arg His Val Arg Gly Trp Leu Gly Met Asp Val Glu Gly Ala His Val
                85                  90                  95

Thr Cys Asp Asn Val Gly Thr Asn Val Pro Leu Gln Val Gly Phe Ser
            100                 105                 110

Asn Gly Val Asp Phe Val Ala Gln Pro Glu Gly Cys Val Leu Thr Asn
        115                 120                 125

Thr Gly Ser Val Val Lys Pro Val Arg Ala Arg Ala Pro Pro Gly Glu
    130                 135                 140

Gln Phe Thr His Ile Val Pro Leu Leu Arg Lys Gly Gln Pro Trp Ser
145                 150                 155                 160

Val Leu Arg Lys Arg Ile Val Gln Met Ile Ala Asp Phe Leu Ala Gly
                165                 170                 175

Ser Ser Asp Val Leu Val Phe Val Leu Trp Ala Gly Gly Leu Glu Leu
            180                 185                 190

Thr Thr Met Arg Tyr Phe Val Lys Ile Gly Ala Val Lys His Cys Gln
        195                 200                 205

Cys Gly Thr Val Ala Thr Cys Tyr Asn Ser Val Ser Asn Asp Tyr Cys
    210                 215                 220

Cys Phe Lys His Ala Leu Gly Cys Asp Tyr Val Tyr Asn Pro Tyr Val
225                 230                 235                 240

Ile Asp Ile Gln Gln Trp Gly Tyr Val Gly Ser Leu Ser Thr Asn His
                245                 250                 255

His Ala Ile Cys Asn Val His Arg Asn Glu His Val Ala Ser Gly Asp
            260                 265                 270

Ala Ile Met Thr Arg Cys Leu Ala Val Tyr Asp Cys Phe Val Lys Asn
        275                 280                 285

Val Asp Trp Ser Ile Thr Tyr Pro Met Ile Ala Asn Glu Asn Ala Ile
    290                 295                 300

Asn Lys Gly Gly Arg Thr Val Gln Ser His Ile Met Arg Ala Ala Ile
305                 310                 315                 320

Lys Leu Tyr Asn Pro Lys Ala Ile His Asp Ile Gly Asn Pro Lys Gly
                325                 330                 335

Ile Arg Cys Ala Val Thr Asp Ala Lys Trp Tyr Cys Tyr Asp Lys Asn
            340                 345                 350

Pro Ile Asn Ser Asn Val Lys Thr Leu Glu Tyr Asp Tyr Met Thr Asn
        355                 360                 365

Gly Gln Met Asp Gly Leu Cys Leu Phe Trp Asn Cys Asn Val Asp Met
    370                 375                 380

Tyr Pro Glu Phe Ser Ile Val Cys Arg Phe Asp Thr Arg Thr Arg Ser
```

```
                385                 390                 395                 400
Thr Leu Asn Leu Glu Gly Val Asn Gly Gly Ser Leu Tyr Val Asn Asn
                    405                 410                 415

His Ala Phe His Thr Pro Ala Tyr Asp Lys Arg Ala Met Ala Lys Leu
                420                 425                 430

Lys Pro Ala Pro Phe Phe Tyr Tyr Asp Asp Gly Ser Cys Glu Val Val
                435                 440                 445

His Asp Gln Val Asn Tyr Val Pro Leu Arg Ala Thr Asn Cys Ile Thr
                450                 455                 460

Lys Cys Asn Ile Gly Gly Ala Val Cys Ser Lys His Ala Asn Leu Tyr
465                 470                 475                 480

Arg Ala Tyr Val Glu Ser Tyr Asn Ile Phe Thr Gln Ala Gly Phe Asn
                    485                 490                 495

Ile Trp Val Pro Thr Thr Phe Asp Cys Tyr Asn Leu Trp Gln Thr Phe
                500                 505                 510

Thr Glu Val Asn Leu Gln
            515

<210> SEQ ID NO 8
<211> LENGTH: 517
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 8

Ala Asn Glu Gly Cys Gly Leu Phe Lys Asp Cys Ser Arg Gly Asp Asp
 1               5                   10                  15

Leu Leu Pro Pro Ser His Ala Asn Thr Phe Met Ser Leu Ala Asp Asn
                20                  25                  30

Phe Lys Thr Asp Gln Tyr Leu Ala Val Gln Ile Gly Val Asn Gly Pro
            35                  40                  45

Ile Lys Tyr Glu His Val Ile Ser Phe Met Gly Phe Arg Phe Asp Ile
        50                  55                  60

Asn Ile Pro Asn His His Thr Leu Phe Cys Thr Arg Asp Phe Ala Met
65                  70                  75                  80

Arg Asn Val Arg Gly Trp Leu Gly Phe Asp Val Glu Gly Ala His Val
                85                  90                  95

Val Gly Ser Asn Val Gly Thr Asn Val Pro Leu Gln Leu Gly Phe Ser
            100                 105                 110

Asn Gly Val Asp Phe Val Val Arg Pro Glu Gly Cys Val Val Thr Glu
        115                 120                 125

Ser Gly Asp Tyr Ile Lys Pro Val Arg Ala Arg Ala Pro Pro Gly Glu
130                 135                 140

Gln Phe Ala His Leu Leu Pro Leu Leu Lys Arg Gly Gln Pro Trp Asp
145                 150                 155                 160

Val Val Arg Lys Arg Ile Val Gln Met Cys Ser Asp Tyr Leu Ala Asn
                165                 170                 175

Leu Ser Asp Ile Leu Ile Phe Val Leu Trp Ala Gly Gly Leu Glu Leu
            180                 185                 190

Thr Thr Met Arg Tyr Phe Val Lys Ile Gly Pro Ser Lys Ser Cys Asp
        195                 200                 205

Cys Gly Lys Val Ala Thr Cys Tyr Asn Ser Ala Leu His Thr Tyr Cys
210                 215                 220
```

-continued

```
Cys Phe Lys Met Ala Leu Gly Cys Asp Tyr Leu Tyr Asn Pro Tyr Cys
225                 230                 235                 240

Ile Asp Ile Gln Gln Trp Gly Tyr Lys Gly Ser Leu Ser Leu Asn His
            245                 250                 255

His Glu His Cys Asn Val His Arg Asn Glu His Val Ala Ser Gly Asp
        260                 265                 270

Ala Ile Met Thr Arg Cys Leu Ala Ile His Asp Cys Phe Val Lys Asn
    275                 280                 285

Val Asp Trp Ser Ile Thr Tyr Pro Phe Ile Gly Asn Glu Ala Val Ile
290                 295                 300

Asn Lys Ser Gly Arg Ile Val Gln Ser His Thr Met Arg Ser Val Leu
305                 310                 315                 320

Lys Leu Tyr Asn Pro Lys Ala Ile Tyr Asp Ile Cys Asn Pro Lys Gly
            325                 330                 335

Ile Arg Cys Ala Val Thr Asp Ala Lys Trp Phe Cys Phe Asp Lys Asn
        340                 345                 350

Pro Thr Asn Ser Asn Val Lys Thr Leu Glu Tyr Asp Tyr Ile Thr His
    355                 360                 365

Gly Gln Phe Asp Gly Leu Cys Leu Phe Trp Asn Cys Asn Val Asp Met
370                 375                 380

Tyr Pro Glu Phe Ser Val Val Cys Arg Phe Asp Thr Arg Cys Arg Ser
385                 390                 395                 400

Pro Leu Asn Leu Glu Gly Cys Asn Gly Gly Ser Leu Tyr Val Lys Asn
            405                 410                 415

His Ala Phe His Thr Pro Ala Phe Asp Lys Arg Ala Phe Ala Lys Leu
        420                 425                 430

Lys Pro Met Pro Phe Phe Tyr Asp Asp Thr Glu Cys Asp Lys Leu
    435                 440                 445

Gln Asp Ser Ile Asn Tyr Val Pro Leu Arg Ala Ser Asn Cys Ile Thr
450                 455                 460

Lys Cys Asn Val Gly Gly Ala Val Cys Ser Lys His Cys Ala Met Tyr
465                 470                 475                 480

His Ser Tyr Val Asn Ala Tyr Asn Thr Phe Thr Ser Ala Gly Phe Thr
            485                 490                 495

Ile Trp Val Pro Thr Ser Phe Asp Thr Tyr Asn Leu Trp Gln Thr Phe
        500                 505                 510

Ser Asn Asn Leu Gln
        515

<210> SEQ ID NO 9
<211> LENGTH: 515
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 9

Val Cys Gly Leu Phe Lys Asn Cys Thr Arg Thr Pro Leu Asn Leu Pro
1               5                   10                  15

Pro Thr His Ala His Thr Phe Leu Ser Leu Ser Asp Gln Phe Lys Thr
            20                  25                  30

Thr Gly Asp Leu Ala Val Gln Ile Gly Ser Asn Asn Val Cys Thr Tyr
        35                  40                  45

Glu Met Val Ile Ser Phe Met Gly Phe Arg Phe Asp Ile Ser Ile Pro
    50                  55                  60
```

```
Gly Ser His Ser Leu Phe Cys Thr Arg Asp Phe Ala Ile Arg Asn Val
 65                  70                  75                  80

Arg Gly Trp Leu Gly Met Asp Val Glu Ser Ala His Val Cys Gly Asp
                 85                  90                  95

Asn Ile Gly Thr Asn Val Pro Leu Gln Val Gly Phe Ser Asn Gly Val
            100                 105                 110

Asn Phe Val Val Gln Thr Glu Gly Cys Val Ser Thr Asn Phe Gly Asp
        115                 120                 125

Val Ile Lys Pro Val Cys Ala Lys Ser Pro Gly Glu Gln Phe Arg
130                 135                 140

His Leu Ile Pro Leu Leu Arg Lys Gly Gln Pro Trp Leu Ile Val Arg
145                 150                 155                 160

Arg Arg Ile Val Gln Met Ile Ser Asp Tyr Leu Ser Asn Leu Ser Asp
                165                 170                 175

Ile Leu Val Phe Val Leu Trp Ala Gly Ser Leu Glu Leu Thr Thr Met
            180                 185                 190

Arg Tyr Phe Val Lys Ile Gly Pro Ile Lys Tyr Cys Tyr Cys Gly Asn
        195                 200                 205

Phe Ala Thr Cys Tyr Asn Ser Val Ser Asn Glu Tyr Cys Cys Phe Lys
    210                 215                 220

His Ala Leu Gly Cys Asp Tyr Val Tyr Asn Pro Tyr Ala Phe Asp Ile
225                 230                 235                 240

Gln Gln Trp Gly Tyr Val Gly Ser Leu Ser Gln Asn His His Thr Phe
                245                 250                 255

Cys Asn Ile His Arg Asn Glu His Asp Ala Ser Gly Asp Ala Val Met
            260                 265                 270

Thr Arg Cys Leu Ala Val His Asp Cys Phe Val Lys Asn Val Asp Trp
        275                 280                 285

Thr Val Thr Tyr Pro Phe Ile Ala Asn Glu Lys Phe Ile Asn Gly Cys
    290                 295                 300

Gly Arg Asn Val Gln Gly His Val Val Arg Ala Ala Leu Lys Leu Tyr
305                 310                 315                 320

Lys Pro Ser Val Ile His Asp Ile Gly Asn Pro Lys Gly Val Arg Cys
                325                 330                 335

Ala Val Thr Asp Ala Lys Trp Tyr Cys Tyr Asp Lys Gln Pro Val Asn
            340                 345                 350

Ser Asn Val Lys Leu Leu Asp Tyr Asp Tyr Ala Thr His Gly Gln Leu
        355                 360                 365

Asp Gly Leu Cys Leu Phe Trp Asn Cys Asn Tyr Asp Met Tyr Phe Glu
370                 375                 380

Phe Ser Ile Val Cys Arg Phe Asp Thr Arg Thr Arg Ser Val Phe Asn
385                 390                 395                 400

Leu Glu Gly Val Asn Gly Gly Ser Leu Tyr Val Asn Lys His Ala Phe
                405                 410                 415

His Thr Pro Ala Tyr Asp Lys Arg Ala Phe Val Lys Leu Lys Pro Met
            420                 425                 430

Pro Phe Phe Tyr Phe Asp Asp Ser Asp Cys Asp Val Val Gln Glu Gln
        435                 440                 445

Val Asn Tyr Val Pro Leu Arg Ala Ser Ser Cys Val Thr Arg Cys Asn
450                 455                 460

Ile Gly Gly Ala Val Cys Ser Lys His Ala Asn Leu Tyr Gln Lys Tyr
465                 470                 475                 480
```

```
Val Glu Ala Tyr Asn Thr Phe Thr Gln Ala Gly Phe Asn Ile Trp Val
                485                 490                 495

Pro His Ser Phe Asp Val Tyr Asn Leu Trp Gln Ile Phe Ile Glu Thr
            500                 505                 510

Asn Leu Gln
        515

<210> SEQ ID NO 10
<211> LENGTH: 196
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

Trp Ile Gly Phe Asp Val Glu Gly Cys His Ala Thr Arg Asp Ala Val
  1               5                  10                  15

Gly Thr Asn Leu Pro Leu Gln Leu Gly Phe Ser Thr Gly Val Asn Leu
             20                  25                  30

Val Ala Val Pro Thr Gly Tyr Val Asp Thr Glu Asn Asn Thr Glu Phe
         35                  40                  45

Thr Arg Val Asn Ala Lys Pro Pro Gly Asp Gln Phe Lys His Leu
 50                  55                  60

Ile Pro Leu Met Tyr Lys Gly Leu Pro Trp Asn Val Val Arg Ile Lys
 65                  70                  75                  80

Ile Val Gln Met Leu Ser Asp Thr Leu Lys Gly Leu Ser Asp Arg Val
                 85                  90                  95

Val Phe Val Leu Trp Ala His Gly Phe Glu Leu Thr Ser Met Lys Tyr
            100                 105                 110

Phe Val Lys Ile Gly Pro Glu Arg Thr Cys Cys Leu Cys Asp Lys Arg
        115                 120                 125

Ala Thr Cys Phe Ser Thr Ser Ser Asp Thr Tyr Ala Cys Trp Asn His
    130                 135                 140

Ser Val Gly Phe Asp Tyr Val Tyr Asn Pro Phe Met Ile Asp Val Gln
145                 150                 155                 160

Gln Trp Gly Phe Thr Gly Asn Leu Gln Ser Asn His Asp Gln His Cys
                165                 170                 175

Gln Val His Gly Asn Ala His Val Ala Ser Cys Asp Ala Ile Met Thr
            180                 185                 190

Arg Cys Leu Val
        195

<210> SEQ ID NO 11
<211> LENGTH: 64
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Ala Phe Glu His Ile Val Tyr Gly Asp Phe Ser His Gly Gln Leu Gly
  1               5                  10                  15

Gly Leu His Leu Met Ile Gly Leu Ala Lys Arg Ser Gln Asp Ser Pro
             20                  25                  30

Leu Lys Leu Glu Asp Phe Ile Arg Met Asp Ser Thr Val Lys Asn Tyr
         35                  40                  45
```

-continued

```
Phe Ile Thr Asp Ala Gln Thr Gly Ser Ser Lys Cys Val Cys Ser Val
    50                  55                  60

<210> SEQ ID NO 12
<211> LENGTH: 168
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 12

Asn Val Ala Lys Tyr Thr Gln Leu Cys Gln Tyr Leu Asn Thr Leu Thr
  1               5                  10                  15

Leu Ala Val Pro Tyr Asn Met Arg Val Ile His Phe Gly Ala Gly Ser
                 20                  25                  30

Asp Lys Gly Val Ala Pro Gly Thr Ala Val Leu Arg Gln Trp Leu Pro
             35                  40                  45

Thr Gly Thr Leu Leu Val Asp Ser Asp Leu Asn Asp Phe Val Ser Asp
         50                  55                  60

Ala Asp Ser Thr Leu Ile Gly Asp Cys Ala Thr Val His Thr Ala Asn
 65                  70                  75                  80

Lys Trp Asp Leu Ile Ile Ser Asp Met Tyr Asp Pro Arg Thr Lys His
                 85                  90                  95

Val Thr Lys Glu Asn Asp Ser Lys Glu Gly Phe Phe Thr Tyr Leu Cys
                100                 105                 110

Gly Phe Ile Lys Gln Lys Leu Ala Leu Gly Gly Ser Ile Ala Val Lys
            115                 120                 125

Ile Thr Glu His Ser Trp Asn Ala Asp Leu Tyr Lys Leu Met Gly His
        130                 135                 140

Phe Ser Trp Trp Thr Ala Phe Val Thr Asn Val Asn Ala Ser Ser Ser
145                 150                 155                 160

Glu Ala Phe Leu Ile Gly Met Thr
                165
```

LIVE ATTENUATED CORONAVIRUS VACCINES

This application claims benefit of priority to U.S. Provisional Application Ser. No. 60/573,587, filed May 21, 2004, the entire contents of which are hereby incorporated by reference.

The government owns rights in the present invention pursuant to grant number 5RO1 A126603-15 of the National Institutes of Health and National Institute Allergy Infectious Disease.

BACKGROUND OF THE INVENTION

1. Field of the Invention

The present invention relates generally to the fields of microbiology, immunology and virology. More particularly, it concerns live, attenuated Coronaviridae vaccines and methods for preventing or limiting Coronaviridae infections.

2. Description of Related Art

Coronaviruses have been long known to cause important diseases in a wide variety of animal species, including humans, cattle, swine, chickens, dogs, cats and mice. Coronavirus diseases in non-human species may be quite severe, and devastating in domestic livestock such as pigs, cattle and chickens. The characterized human coronaviruses—HCoV-229E and HCoV OC43—are significant causes of upper respiratory infections, responsible for 10-35% of human colds. Studies of human coronaviruses have been limited by their lack of growth in culture from primary isolates, and by the lack, until recently, of reverse genetic approaches for their study. Thus, while the human coronaviruses are arguably two of the most economically important viruses in humans, ongoing research has been pursued only by a handful of dedicated investigators.

The emergence of a new human coronavirus associated with "severe acute respiratory syndrome" (SARS) surprised many scientists and public health officials, but has highlighted characteristics of coronaviruses well known to investigators. The coronaviruses have high rates of mutagenesis and homologous RNA recombination. In fact, template switching and recombination are essential to the normal life cycle of the viruses. In addition, the species barrier for coronaviruses has been predicted to be tenuous. Studies of coronaviruses in culture have demonstrated the ability of coronaviruses to adapt for replication in cells of different species. In addition, some studies have demonstrated that the murine coronaviruses may cause disease in primates following direct inoculation into brain. Finally, coronaviruses have been proposed, based on evolutionary studies, to have acquired genes from other viruses or cells, probably by recombination events. The emergence of a new coronavirus pathogenic for humans, by either adaptation of an animal virus, or by recombination of two coronaviruses during a coinfection, is consistent with these features of coronavirus evolution, replication and maintenance in populations.

Vaccine approaches for important domestic animal coronaviruses diseases, specifically the chicken avian infectious bronchitis virus (E3V), porcine transmissible gastroenteritis virus (TGEV), canine coronavirus (CCV), bovine coronavirus (BCV) and feline infectious peritonitis virus (FIPV), have been developed or attempted over the past 20 years. The approaches to vaccine development have been based on non-targeted natural attenuation, virus expression vectors, virus inactivation, recombinant viral structural proteins, and novel approaches to deliver or adjuvant vaccines. Responses and protectivity of these vaccines have varied widely, but no vaccine has been shown to possess all of the characteristics of safety, stability and efficacy.

For FIPV, live-attenuated, inactivated, and subunit vaccines based on recombinant or purified spike protein, have not only failed to protect against FIPV disease, but have resulted in immune enhancement of infection and disease, a response disturbingly reminiscent of the result following vaccination of humans with inactivated vaccines for measles and respiratory syncytial virus. The most useful animal coronavirus vaccine has been the live-attenuated vaccine for IBV. However, efficacy is still clearly less than optimal. In addition, reversion to virulence may occur, and recombination of the vaccine strain with wild-type viruses has occurred, with disease in chickens caused by the recombinant vaccine-wild-type viruses.

For the most part, vaccines have not been pursued in the past for human coronaviruses, likely because the frequency and severity of infections could not be well defined, and the determinants for protection have not been identified. It is also known that 229E and OC43 can re-infect humans, possibly as often as every other year, suggesting that vaccine strategies may need to be targeted toward limitation of disease severity, since prevention may not be possible.

Together, the known biological properties of coronaviruses, as well as the concerns with limited protection or immune enhancement of disease by coronavirus vaccines, are compelling arguments for a new approach in the development of live, attenuated vaccines that are less subject to reversion and recombination, but possess normal pathways for infection and immune response. This need is all the more critical in light of the emerging human SARS situation.

SUMMARY OF THE INVENTION

Thus, in accordance with the present invention, there is provided a live, attenuated virus of the family Coronaviridae, wherein the virus is characterized as comprising a genome encoding an ExoN comprising a substitution at tyrosine$^{6398}$ of MHV-A59, or an analogous position thereof. The virus may be a group 2 coronavirus, and the genome further encodes an Orf2a polypeptide comprising a substitution at leu$^{106}$ of MHV-A59, or an analogous position thereof. The virus may be a coronavirus or a torovirus, including coronaviruses such as avian infectious bronchitis virus, bovine coronavirus, canine coronavirus, feline infectious peritonitis virus, human coronavirus 229E, human coronavirus OC43, murine hepatitis virus, porcine epidemic diarrhea virus, porcine hemagglutinating encephalomyelitis virus, porcine transmissible gastroenteritis virus, rat coronavirus, turkey coronavirus, severe acute respiratory syndrome virus, or rabbit coronavirus, and toroviruses such as Berne virus or Breda virus.

The virus may further comprise a mutation in least one polyprotein proteinase cleavage site that exhibits reduced as compared to wild-type or no cleavage, such as a C1-C14 cleavage site, or a MHV p28-p65 or p65-p210 cleavage site or analogous position thereof. The cleavage site may comprise an amino acid deletion, an amino acid insertion or an amino acid substitution. Alternatively, the cleavage site may be wild-type, but cleavage may be reduced or eliminated by an allosteric mutation. The tyrosine$^{6398}$ substitution may be a non-conservative substitution, or a histidine in particular. The leu$^{106}$ substitution may be a non-conservative substitution, or a proline in particular. The virus genome may further encodes a mutation in one or more of nsp1, nsp2, nsp3, nsp4, nsp5, nsp6, nsp7, nsp8, nsp9, nsp10, nsp11, nsp12, nsp13, nsp15 or nsp16 coding region.

In another embodiment, there is provided a method of inducing an anti-viral immune response in a host comprising administering to the host a live, attenuated virus vaccine of the family Coronaviridae, wherein the virus is characterized as comprising a genome encoding an ExoN comprising a substitution at tyrosine$^{6398}$ of MHV-A59, or an analogous position thereof. The virus may be a group 2 coronavirus, and the genome further encodes an Orf2a polypeptide comprising a substitution at leu106 of MHV-A59, or an analogous position thereof. The virus may be a coronavirus or a torovirus, including coronaviruses such as avian infectious bronchitis virus, bovine coronavirus, canine coronavirus, feline infectious peritonitis virus, human coronavirus 229E, human coronavirus OC43, murine hepatitis virus, porcine epidemic diarrhea virus, porcine hemagglutinating encephalomyelitis virus, porcine transmissible gastroenteritis virus, rat coronavirus, turkey coronavirus, severe acute respiratory syndrome virus, or rabbit coronavirus, and toroviruses such as Berne virus or Breda virus. The vaccine may be administered intravenously or subcutaneously, and/or co-administered with an immunostimulant. The host may be a dog, a cow, a pig, a cat, a mouse, a rat, a horse, a chicken, a turkey, a monkey or a human.

The method may comprise a virus that further comprises a mutation in least one polyprotein proteinase cleavage site that exhibits reduced as compared to wild-type or no cleavage, such as a C1-C14 cleavage site, or a MHV p28-p65 or p65-p210 cleavage site or analogous position thereof. The cleavage site may comprise an amino acid deletion, an amino acid insertion or an amino acid substitution. Alternatively, the cleavage site may be wild-type, but cleavage may be reduced or eliminated by an allosteric mutation. The tyrosine$^{6398}$ substitution may be a non-conservative substitution, or a histidine in particular. The leu$^{106}$ substitution may be a non-conservative substitution, or a proline in particular. The virus genome may further encodes a mutation in one or more of nsp1, nsp2, nsp3, nsp4, nsp5, nsp6, nsp7, nsp8, nsp9, nsp10, nsp11, nsp12, nsp13, nsp15 or nsp16 coding region.

In yet another embodiment, there is provided a coronavirus genome, the genome encoding an ExoN polypeptide comprising a substitution at tyrosine$^{6398}$ of MHV-A59, or an analogous position thereof. Also provided is a coronavirus ExoN polypeptide comprising comprising a substitution at tyrosine$^{6398}$ of MHV-A59, or an analogous position thereof.

In still yet another embodiment, there is provided a vaccine comprising (a) a live, attenuated virus of the family Coronaviridae, the virus characterized as comprising a genome encoding an ExoN polypeptide comprising comprising a substitution at tyrosine$^{6398}$ of MHV-A59, or an analogous position thereof, and (b) a pharmaceutically acceptable diluent. The vaccine may be formulated as a unit dose of $10^6$ to $10^{14}$ infectious particles. The vaccine may be provided in unit dose is provided in a 100 ml aliquot. The vaccine may further comprise a preservative. The vaccine may be lyophilized.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the inherent variation of error for the device, the method being employed to determine the value, or the variation that exists among the study subjects.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. Schematic of the SARS-CoV genome. 30 kb, single-stranded, plus-strand RNA genome is shown, including leader RNA, 20 kb replicase gene, and general organization of structural and accessory genes, including those encoding spike (S), envelope protein, (E), membrane (M), and nucleocapsid proteins (N). Vertical black bars are intergenic regions and transcriptional regulatory sequences. FIG. 1B. Replicase gene organization, protein domains, and mature and intermediate processing products. The nonstructural protein number (nsp), predicted size in kDa, and names or putative functions of proteins are shown for SARS-CoV: PLP2—papain-like proteinase orthologous to MHV PLP2; MP1 and MP2—hydrophobic membrane proteins; 3C-3C-like proteinase; POL—putative RNA-dependent RNA polymerase; HEL—RNA ATPase/helicase; ExoN—putative exonuclease; XendoU—predicted poly(U)-specific endoribonuclease; 2'-O-MT—predicted 2'-O-methyltransferase. For MHV, nsp numbers have not been assigned or are controversial. For this proposal, nsp numbers will correspond to those of SARS-CoV. PLP and regions of the polyprotein cleaved by PLP are shaded in yellow. 3Clpro and regions cleaved by 3Clpro in green. Red bars between genomes—possible intermediate precursor proteins. Black bars,—mature replicase proteins.

Figure 2:
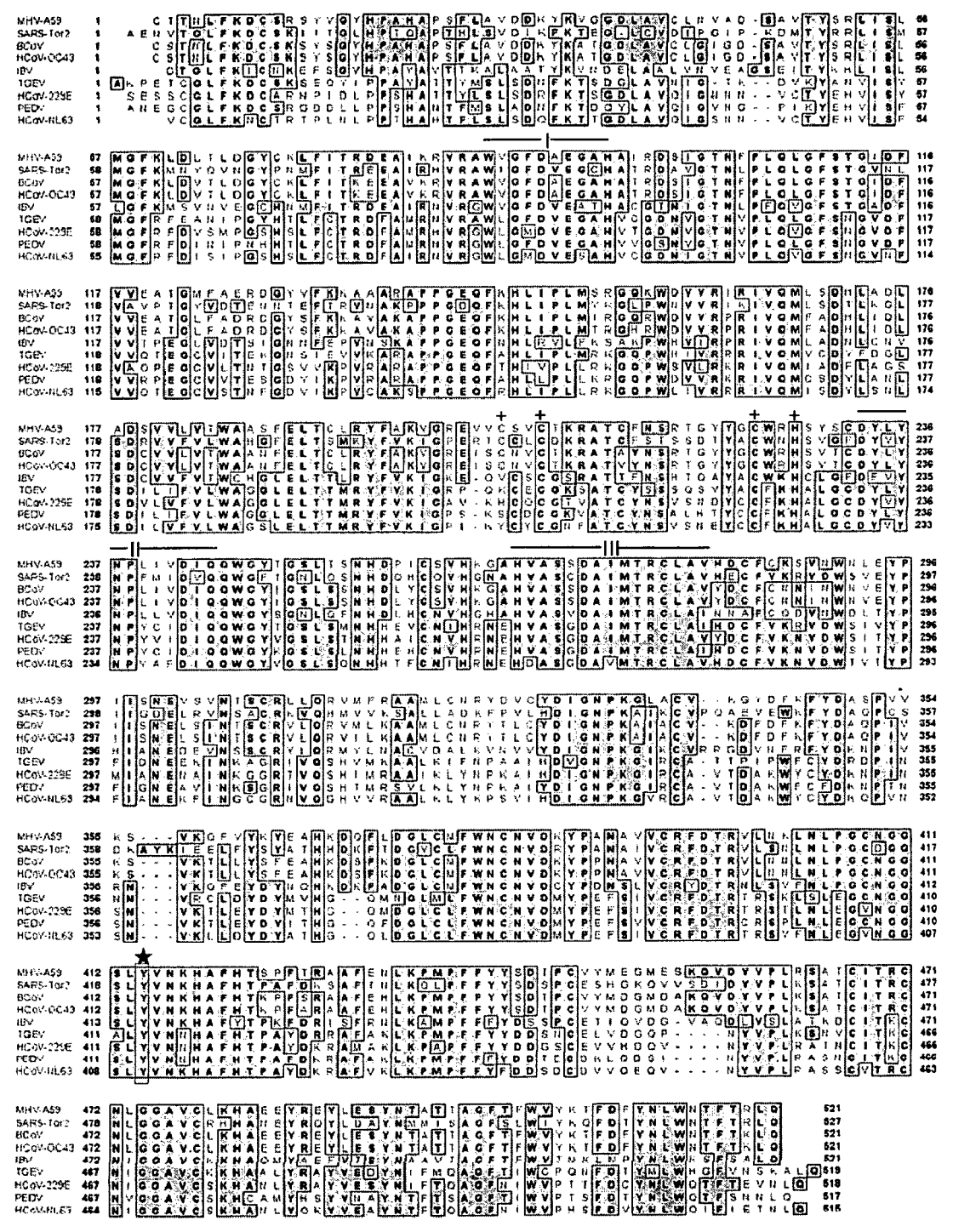

FIG. 2 - Alignment of p59 (nspl14, Exo N) proteins of coronaviruses and conservation of Tyr6398 residue. Alignments were perfonned of available group 1, 2 and 3 coronaviruses using a Clustal W protein alignment (implemented in MacVector 7.1- Accelerys). MHV-A59 - mouse hepatitis virus; SARS-Tor2 - Tor 2 strain of Severe Acute Respiratory Syndrome Coronavirus; BCoV - bovine coronavirus; HCoV - 0C43 -human coronavirus 0C43; JBV - infectious bronchitis virus; TGEV - transmissible gastroenteritis virus of pigs; HCoV-229E - human coronavirus 229E; PEDV - porcine enteric diarrhea virus; HCoV-NL63 - human coronavirus NL63. The location of ORFib Tyr6398 (p59 Tyr4l4) is indicated by box and star. Potential active residues are indicated by regions (horizontal bars) and zinc fingers by +(SEQ. ID NOS: 1-9).

FIGS. 3A-B - Mutations in nsp14 (ExoN) attenuate virulence in mice. (FIG. 3A) Schematic of genome is shown, with enlargement of nsp14 (p59-ExoN) and ORF2a protein (Pro$_{106}$). Nt and aa sequence of published MHV sequences, and those of sequenced virulent A59 strains is shown in the boxes. Changes identified in clones and virus sequence of "uncorrected" icwt are shown by nt and aa sequence. (FIG. 3B). LD$_{50}$ data on mice infected ic with viruses as shown for "uncorrected icwt" and corrected for nsp14 and ORF2A proteins, alone and together.

FIGS. 5A-E - Mutations approaches and sequences of nsp14, nsp15 and nsp16. (FIG. 5A) Organization of proteins and introduction of stop codons beginning in nsp16 toward nsp14: yellow-"midprotein" allowing partial translation and cleavage; red -change initial residue to stop codon. (FIG. 5B) Cleavage site mutations from Aim 1 (grey boxes) and introduction of inactivation cleavage sites (white boxes with arrows). (FIGS. 5C-E) Core sequences with conserved residues with subscript residue numbers in pp1ab. For nsp 14, putative metal finger is underlined (SEQ ID NOS:10-12).

DESCRIPTION OF ILLUSTRATIVE EMBODIMENTS

Figure 1:
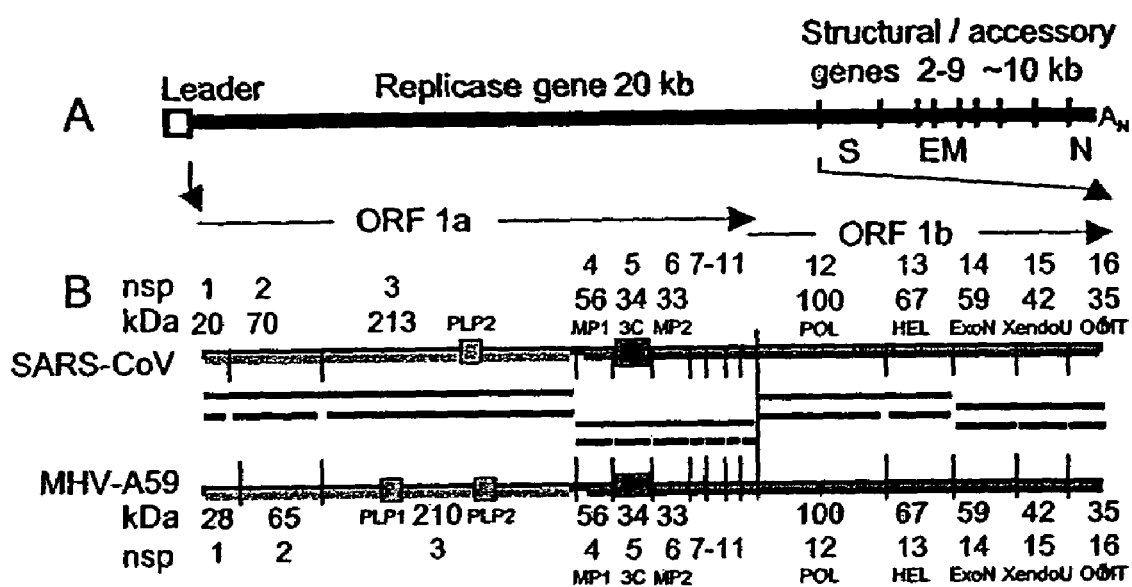
FIGS. 1A-B - Genome organization, replicase proteins, and processing of SARS-CoV and MHV.
Figure 4:
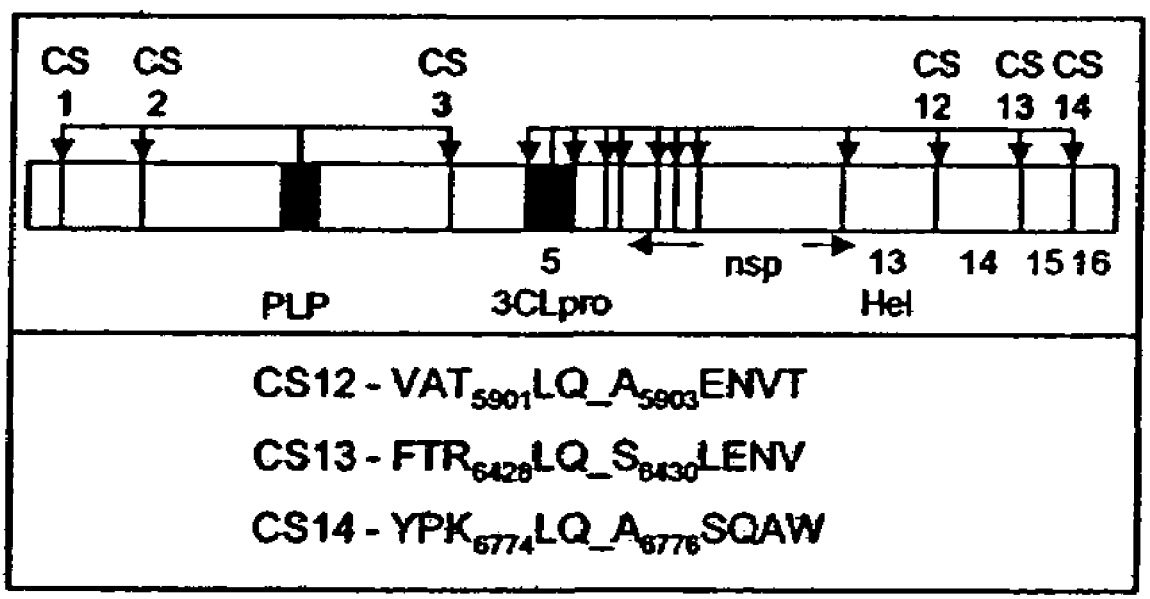
FIG. 4 - Location and sequence of 3CLpro cleavage sites. CS11, 12, and 13. Schematic of 1a/b polyprotein shows PLP and 3CLpro cleavage sites, with location of CS11, 12, and 13. Amino acid sequence flanking cleavage sites is shown, with LQ_(S,A) indicating cleavage between Q and S or A.

Coronaviruses are common pathogens for respiratory, enteric, and neurologic diseases in humans and animals. It has been estimated that coronaviruses are responsible for up to 30% of common colds in humans, and they cause economically significant diseases in domestic animals including cows, chickens, swine, and cats. Group 2 viruses include mouse hepatitis virus (MHV), human coronavirus OC-43, and bovine coronavirus, and the recently identified severe acute respiratory syndrome-associated coronavirus (SARS-CoV) appears to be closely related to the group 2 coronaviruses. Thus, there is considerable interest in the development of vaccines against coronaviruses generally, and against SARS-CoV in particular.

I. The Present Invention

The present inventors isolated an attenuated infectious clone virus produced using an MHV reverse genetics system, and identified two unique mutations in different coding regions of the viral genome. By assembling several infectious clone viruses with each mutation corrected individually and simultaneously, they demonstrated that these mutations both independently and in combination attenuate virulence in mice, while not displaying any distinctive phenotypes, and specifically no inhibition of growth, in DBT cell culture relative to lab strain MHV-A59. One of the mutations, leading to a leucine to proline change at amino acid 106 in the Orf2a protein, was only partially attenuating in the absence of any other changes. The second mutation, a tyrosine to histidine change at amino acid 6398 in the Orf1a/b polyprotein (p59), was completely attenuating independently or in combination with the first mutation.

Neither of these mutations affected virus growth in DBT cells, though there was evidence of replication defects in mice for the attenuated viruses. Interestingly, both of the attenuating mutation sites are located outside of the known virulence- or tropism-associated loci of MHV: S, M, N, and HE. These attenuating mutations are also not located in known structural proteins. There have been previous suggestions that genes outside of S and the structural proteins might be involved in mediating pathogenic properties, but this is the first demonstrations of specific lesions of such. Significantly, the discovery of these attenuating mutations should be applicable to other coronaviruses, as all coronaviruses conserve the tyrosine residue in their p59 homologous protein in Orf1b.

The discovery of two randomly generated mutations in the cDNA of the infectious clone, which were independently and simultaneously attenuating in mice but caused no observed phenotype in cell culture, was very surprising. The inventor's hypothesis is that these mutations were selected for during passage of the F clone plasmid in E. coli cells. Experience during cloning with this plasmid suggested that it was not stable in bacteria. Following correction of nt 19400 and growth of the plasmid in E. coli cells, the mutation would occasionally spontaneously revert. To stabilize the F fragment, it was subcloned it into pSMART-LCAmp vector (Lucigen), which resulted in increased stability of the F clone.

The attenuated viruses described herein have the key features of (a) replicating to high titers in culture (>$10^8$ pfu/ml), (b) diminished replication in animals, and (c) failure to cause disease or illness. The main potential drawback for any live-attenuated vaccine development in coronaviruses is the possibility of reversion or recombination that might restore a virulent phenotype or alter host cell tropism and disease. One possible approach to avoid or overcome this problem is the identification and introduction of multiple attenuating mutations spaced throughout the genome of the virus. Multiple mutations could be introduced singly or in combinations by introducing them on different cDNA fragments. The presence of the multiple mutations would guard against the risk of losing attenuation due to single recombination events or single-site reversions. It would also maintain or introduce attenuating mutations in any recombinant viruses that might be generated by recombination between different coronaviruses.

For human viruses acquired by the respiratory route, live-attenuated vaccines impaired in protein processing would have several potential advantages. Because there is no alteration in the viral structural glycoproteins, it is predicted that replicase protein cleavage mutants would have normal "wild-type" transmission, tropism, attachment, entry and uncoating, and thus could theoretically be administered by oral, intranasal or inhaled approaches. The initial replication and spread from the respiratory epithelium and lymphoid organs also allows for the development of both systemic and mucosal inmmunity.

Furthermore, studies with other animal coronavirus vaccines suggest that viral replication may be necessary for protection from virus challenges. The use of a virus with multiple virulence-attenuating mutations avoids concerns about atypical infections with wild-type viruses following vaccination with inactivated viruses or purified viral proteins, such as occurred with measles virus and respiratory syncytial virus, and also seen with the vaccines for the feline coronavirus, FIPV. Most importantly, the use of a live-attenuated virus allows for both humoral and cellular immunity.

II. Coronaviridae

Viruses in this family infect hosts in the Domain Eucarya, Kingdom Animalia, Phylum Chordata, Subphylum Vertebrata, Classes Mammalia and Aves, Orders Primates, Carnivora, Perissodactyla, Artiodactyla, Rodentia, and Lagomorphia. It is transmitted by means not involving a vector. Worldwide distribution is likely.

Virions are enveloped, slightly pleomorphic, spherical or kidney shaped, and about 120-160 nm in diameter. Surface projections of envelope are distinct, club-shaped, spaced widely apart and dispersed evenly over all the surface. Nucleocapsids are rod-shaped (straight or bent), about 9-13 nm in diameter. Virions associated RNA nucleocapsids exhibit helical or tubular symmetry.

Molecular mass (Mr) of the virion 400×106. Buoyant density is 1.23-1.24 g cm-3 in CsCl, and 1.15-1.19 g cm-3 in sucrose. The sedimentation coefficient is 300-500S. Under in vitro conditions, virions are stable in acid environment (pH 3), relatively stable in presence of Mg$^{++}$. Virions are sensitive to heat, lipid solvents, non-iomc detergents, formaldehyde, and oxidizing agents.

Virions contain one molecule of linear positive-sense single stranded RNA with a total genome length is 20,000-33,000 nt. The 5' end of the genome has a cap, and the 3' end has a poly(A) tract. Subgenomic mRNA is found in infected cells.

Five structural virion proteins found ranging is size between 18,0000 and 220,000 Da. The first is the surface glycoprotein or spike (S) protein. The S protein is responsible for attachment to cells, hemagglutination and membrane fusion. It has a carboxy-terminal half with a coiled-coil structure. The second largest protein (30,000-35,000 Da) is the integral membrane protein (M) which spans the virus envelope three times, with only 10% protruding at the virion surface. The third largest protein (50,000-60,000 Da) is the nucleocapsid protein (N). The fourth largest protein (65,000 Da) is the hemagglutinine-esterase protein (HE), which forms short surface projections, and can have receptor binding, hemagglutination and receptor destroying activities. The fifth largest protein (10,000-12,000 Da) is tentatively designated as the small membrane protein (sM), detected in avian infectious bronchitis virus (IBV) and porcine transmissible gastroenteritis virus (TGEV).

The virus exhibits distinct antigen determinants on envelope and spikes, those corresponding to each of the major structural glycoproteins—S, HE, M, and N. Antigenic specificity of virion can be determined by neutralization tests (S and HE), or complement fixation tests (M). Protective immunity is induced in form of complement independent neutralizing antibodies.

The Coronaviridae family is split into two groups—coronavirus and torovirus. Coronaviruses include avian infectious bronchitis virus, bovine coronavirus, canine coronavirus, feline infectious peritonitis virus, human coronavirus 229E, human coronavirus OC43, murine hepatitis virus, porcine epidemic diarrhea virus, porcine hemagglutinating encephalomyelitis virus, porcine transmissible gastroenteritis virus, rat coronavirus, turkey coronavirus, severe acute respiratory syndrome virus, rabbit coronavirus, or the recently identified SARS associated human coronavirus. Toroviruses include Berne virus or Breda virus.

III. Targets for Attenuating Mutations

In accordance with the present invention, attenuating mutations have been identified in the p59 and Orf2a proteins of MHV-A59. The p59 residue (Tyr6398) (also referred to as nsp14 and Exo N) is one of many residues in the replicase that are 100% conserved across all coronaviruses, and therefore provide the basis for making similar changes in analogous residues of the other coronaviruses. In addition, such mutations may be combined into a single virus, and with other mutations in structural and non-structural genes. The p59 and Orf2a proteins, as well as other targets, are described below.

A. Nsp14/p59 (ExoN)

The p59 protein if part of the complex polyprotein, described in greater detail below. No function has been demonstrated for this protein, though this highly conserved protein is predicted to be an exoribonuclease (ExoN) of the DEDD superfamily of exonucleases. This prediction is based on primary amino acid sequence identity of three motifs containing the putative catalytic aspartic and glutamic acid residues necessary for the exonuclease activity.

The virulence-associated tyrosine/histidine residue is located in a region 140 amino acids carboxy-terminal to the last predicted ExoN catalytic motif. Analysis of deduced amino acid sequences of all genome-sequenced coronaviruses shows increasing identity across the carboxy-terminal half of the ORF 1a polyprotein and all of ORF1b polyrpotein. Specifically, up to 60% to 80% identity is observed across putative fuictional proteins such as the RNA-dependent RNA polymerase (RdRp, pol, nsp12), the ATPase/helicase (hel, nsp14, p67). Further, the amino acid identity within proteins is focused in regions or motifs. However for proteins with predicted functions, the predictions were based on organization or sequences discrete regions, and thus the identity across the remainder of the proteins is of unknown significance in protein function, viral replication or viral pathogenesis. This suggests that many of these regions of identity may play identical conserved roles, but distinct from the predicted functions.

B. Orf2a

The Orf2a protein also has no known function. It has been reported to be a non-structural protein that is cytosolic and non-membrane associated. The Orf2a protein was shown to be non-essential for MHV replication in cell culture, and its deletion did not affect growth, RNA synthesis, or protein expression, leading to the suggestion that its functional role may only be manifest in vivo. It is predicted to be a cyclic phosphodiesterase (CPD), another RNA processing enzyme associated with tRNA maturation.

The mutated leucine residue is located in the Orf2a protein, of group 2 coronaviruses including, including MHV, OC43, and BCoV. The leucine residue is conserved among those viruses that possess the Orf2a protein. However, the mutation is not associated with the predicted catalytic residues of the putative enzyme. While this ORF and protein is not conserved among all coronaviruses, there are several medically and agriculturally important viruses in this group. In addition, the fact the ORF 2a mutation is independently attenuating in animals but has no independent or synergistic impact on replication in culture suggests that mutations in both conserved and non-conserved ORFS of different group coronaviruses will aid efforts to introduce multiple mutation across the genome that stabilize against or eliminate reversion to virulence or recombination.

C. Nsp15/XendoU

The prediction of nsp15 as a XendoU ortholog (poly(U)-specific endoribonuclease) is based on alignment of a small number of identical and similar residues within a region of the predicted protein sequence. Since active site residues for XendoU proteins have not been defined, the prediction is both tenuous and difficult to prove biochemically. However, the predictions do identify residues that are highly conserved in the coronavirus proteins and relatively with other non-viral proteins known to have XendoU function. These glycine, histidine, and lysine residues may be substituted with alanine and with conservative and non-conservative residues.

D. Nsp16/2' O-methyltransferase.

The 2'-O-MT activity of nsp16 was predicted based on alignment of residues with those of known proteins with methyltransferase function, specifically the RrmJ family. However, this is only a subset of the critical residues of the known enzymes and thus establishment of O-MT activity will require experimental confirmation of function. At this time, it is unclear if this protein actually methylates the RNA cap, the penultimate nucleotide, or both within the genome. For SARS-CoV nsp16, lys$^{6821}$, lys$^{6945}$, and asp$^{6905}$ have been proposed to be the site of a catalytic triad. Mutations may be introduced at lys$^{6821}$, lys$^{6945}$, and asp$^{6905}$, and will include both conservative and non-conservative changes; for Lys these will include alanine, histidine, arginine, and proline; for asp, substitutions include alanine, asparagine, glutamic acid, histidine, and proline. Other potential mutatable residues are conserved in the RrmJ family and between coronaviruses and include leu$^{6936}$, gly$^{6940}$, glu$^{6978}$, and gly$^{6983}$. Since coronaviruses appear to mediate all stages of their mRNA synthesis in the host cell cytoplasm, presumably including addition of methylguanosine caps to mRNAs, nsp16 is an attractive target for a specific function in viral replication. If, in fact, nsp16 is involved in mRNA capping, then it would possess a presumably critical activity, and alteration of residues known to be required for MT activity of known enzymes would likely reduce or abolish this activity.

E. Replicase Polyprotein Cleavages Sites

1. Gene and Protein Structure

The coronavirus replicase gene (also known as gene 1 or the polymerase gene) comprises 22 kB of the coronavirus genome, corresponding to some 7800 amino acids, and is composed of two overlapping open reading frames—ORF1a and 1b. Following uncoating of the RNA genome in the cell cytoplasm, the replicase gene is translated as either an ORF la polyprotein (495 kD) or as an ORF1ab fusion polyprotein (803 kD), with translation of ORF 1b requiring a ribosomal frameshift event at the end of ORF 1 a. The intact replicase polyproteins are not detected during natural infection, since maturation proteolytic cleavages occur cotranslationally by three proteinase functions encoded in ORF la polyprotein. The proteolytic processing results in 15 mature proteins, including the proteinases, an RNA helicase, and a putative RNA-dependent RNA polymerase. The MHV proteins are set forth in Table 1.

TABLE 1

MHV Replicase Polyproteins

| Protein Designation | Residues | Function |
|---|---|---|
| p28 | 1-247 | Unknown; localizes to replication complexes early in infection where it associates with membranes by easily disrupted peripheral mechanisms |
| p65 | 248-834 | Unknown; shown to associate throughout infection with membranes of replication complexes at sites of viral RNA synthesis, likely by interactions with other proteins |
| P210 | 833-2837 | Encodes a protein with two papain-like proteinase domains that cleave the first three (C1-C3) cleavage sites |
| MP1 | 2838-3332 | Highly hydrophobic, membrane associated, found in replication complexes |
| 3CLpro | 3333-3633 | Picornain like proteinase responsible for cleavage at C4-C14 |
| MP2 | | Highly hydrophobic, membrane associated, localization in cells unknown |
| p10 | | Associates with p22, p12, p15 in replication complexes |
| p22 | | Associates with p10, p12, p15 in replication complexes |
| p12 | | Associates with p22, p10, p15 in replication complexes |
| p15 | | Associates with p22, p12, p10 in replication complexes |

TABLE 1-continued

MHV Replicase Polyproteins

| Protein Designation | Residues | Function |
|---|---|---|
| Polymerase (pol, p100) | | Putative RNA dependent RNA polymerase, localizes to replication complexes |
| Helicase (hel, p67) | | RNA unwinding and NTPase activities |
| p57 | | Unknown |
| p42 | | Unknown |
| p33 | | Unknown |

The replicase gene expresses all of the viral factors required for all stages of MHV mRNA synthesis and replication. In addition, it has been shown that inhibition of polyprotein processing at any time during infection results in rapid shutoff of viral RNA synthesis, indicating that at least some of the proteolytic processing events are required for RNA synthesis. However there are differences in mature replicase proteins among different coronaviruses, particularly in the amino-terminal 100 kD of the polyproteins.

2. Cleavage Sites

By convention, the present invention identifies the polyprotein cleavage sites as C1-C14. These sites are defined as cleaving between adjacent products. Examples for MHV are set forth in Table 2, below.

TABLE 2

Replicase Polyprotein Cleavage Sites

| Cleavage Site | Upstream Protein | Downstream Protein |
|---|---|---|
| C1 | p28 | p65 |
| C2 | p65 | p210 |
| C3 | P210 | MP1 |
| C4 | MP1 | 3C |
| C5 | 3C | MP2 |
| C6 | MP2 | p10 |
| C7 | p10 | p22 |
| C8 | p22 | p12 |
| C9 | p12 | p15 |
| C10 | p15 | Polymerase |
| C11 | Polymerase | Helicase |
| C12 | Helicase | p57 |
| C13 | p57 | p42 |
| C14 | p42 | p33 |

The third protein processed from the replicase polyprotein is p210 (Schiller et al., 1998). The p210 protein incorporates amino acids 833 to a predicted carboxy-terminus at amino acid 2837, with a predicted mass of 221 kD. p210 contains the two papain-like proteinase domains (PLP1 and PLP2) that have been shown to cleave the first three cleavage sites (CS1, CS2 and CS3) at the carboxy-termini of p28, p65 and p210, respectively. The apparent difference between coronaviruses in the predicted number of proteinases, and the differences in the size and number of proteins in the amino-terminal half of the polyprotein, was interpreted to indicate a lack of common critical functions in this region of gene. A recent study used sequence comparisons, parsimony analyses, and studies of the cleavage sites and proteinase functions to compare the coronavirus p210 and the corresponding p195 proteins of the human coronavirus 229E (HCoV-229E) and infectious bronchitis virus (IBV) (Ziebuhr et al., 2001). The analyses identified common domains of the coronavirus p210/p195 proteins (FIG. 2), several of which had previously been predicted or confirmed for MHV (Lee et al., 1991). The amino-terminal domain of p210 was referred to as the "acidic domain" (Ac) based on the concentration of acidic residues. The PLP1 domain consists of the sequence required for proteinase activity during in vitro cleavage reactions (Bonilla et al. 1995). The X domain is a region of increased conservation among the different coronavirus p210/p195 proteins with no known or predicted functions (Lee et al., 1991). The functional PLP2 domains are a variable distance from the X domains, and have been less completely characterized as to their functional requirements. Both PLP1 and PLP2 have been demonstrated to function with a catalytic dyad of Cys and His residues (Baker et al., 1993; Bonilla et al., 1995; Kanjanahaluethai and Baker, 2000). Finally, a Y domain consists of a region incorporating two stretches of predominantly hydrophobic residues that predict membrane-spanning helices (Lee et al., 1991).

Coronavirus PLPs have a zinc finger motif in the predicted papain-like fold of the enzymes, with predicted similarities to the human transcription elongation factor TFIIS (Herold et al., 1999). The zinc finger has been shown to bind zinc, which is required for PLP function in vitro. Mutations in this motif abolish proteolytic activity. It has been suggested based on these features and demonstrated contributions of the zinc finger to RNA synthesis in the arterivirus, equine arteritis virus (EAV) (Tijms et al., 2001), that the zinc finger may serve functions in addition to PLP proteolytic activity.

Studies of PLP1 and PLP2, as well as identification and detailed mutagenesis of replicase polyprotein cleavage sites, have been performed in vitro. PLP1 has been shown to proteolytically process the first two cleavage sites in the MHV replicase polyprotein: between p28 and p65 at 247G/V248 (referred to as CS1) and between p65 and p210 at 832A/G833 (CS2) (Dong and Baker, 1994; Hughes et al., 1995; Bonilla et al., 1997; Baker et al., 1993). PLP2 has been shown to cleave at the carboxy-terminus of p210 (CS3), likely in a cis autocat (Kanjanahaluethai and Baker, 2000; Kanjanahaluethai et al., 2001). Although the MHV CS3 cleavage site has not been reported, by direct comparison with identified IBV PLP2 cleavage site the MHV-A59 p210 carboxy-terminal cleavage (CS3) would be predicted to be 2837G/A2838. Analysis of the MHV CS1 and CS2 in comparison with other group 1 coronaviruses (TGEV, HCoV-229E) (Elcouet et al., 1995; Herold et al., 1993), group 2 coronaviruses (MHV-JHM, BCV) (Yoo and Pei, 2001; Chouljenko et al., 2001), and group 3 coronaviruses (IBV) (Boursnell et al., 1987), has demonstrated similarities at the P1/P1' cleavage dipeptides; Gly or Ala at P1 of all coronavirus PLP CS, and Val, Ala or Gly at P1'. HCoV is the exception, using Asn in the P1' position. Overall, P5, P2, P1 and P1' have been most intolerant of changes, with mutations at these sites disrupting cleavage in vitro.

Analysis of the coronavirus PLPs and their cognate cleavage sites suggests that PLP1 and PLP2 are paralogous proteinases, originating from a common coronavirus or pre-coronavirus ancestor, and that they have diverged over time (Ziebuhr et al., 2001) (FIG. 3). For example, all coronaviruses except IBV express both PLP1 and PLP2 activities and share the common feature that PLP1 cleaves CS1 and CS2. IBV only expresses a PLP2 that cleaves at a single site equivalent to CS2. In IBV, a functional PLP1 is not detected, whereas a residual, highly altered and inactive PLP 1 domain has recently been identified by sequence comparison (Ziebuhr et al., 2001). These observations have led to the hypothesis that there may be overlap of cleavage site specificity and PLP activity, and possible redundancy of cleavage activity, with PLP 2 able to mediate cleavages at PLP1 cognate sites. This has been demonstrated to be true for HCoV, with both PLP1 and PLP2 able to cleave CS2 in vitro (Ziebuhr et al., 2001). In fact, the data suggest that the "normal" CS2 cleavage event may involve the cooperative activity of PLP1 and PLP2. However, it was also demonstrated that when PLP 1 was catalytically inactivated, PLP2 was able to independently mediate CS2 cleavage in vitro.

IV. Engineering of Coronaviridae Genomes

Thus, in accordance with the present invention, it will be desirable to create a variety of different mutants in Coronaviridae proteins. Mutagenesis is the process whereby changes occur in the structure of a genome. Mutation can involve modification of the nucleotide sequence of a single gene, blocks of genes or a whole chromosome. Changes in single genes may be the consequence of point mutations which involve the removal, addition or substitution of a single nucleotide base within a DNA sequence, or they may be the consequence of changes involving the insertion or deletion of large numbers of nucleotides.

Mutations can arise spontaneously as a result of events such as errors in the fidelity of DNA replication or the movement of transposable genetic elements (transposons) within the genome. They also are induced following exposure to chemical or physical mutagens. Such mutation-inducing agents include ionizing radiations, ultraviolet light and a diverse array of chemical such as alkylating agents and polycyclic aromatic hydrocarbons all of which are capable of interacting either directly or indirectly (generally following some metabolic biotransformations) with nucleic acids. The DNA lesions induced by such environmental agents may lead to modifications of base sequence when the affected DNA is replicated or repaired and thus to a mutation. Mutation also can be site-directed through the use of particular targeting methods. Any number of different mutagenic approaches may be taken, as described below.

A. Coronaviridae Genomes

One of skill in the art may use various Coronaviridae sequences to design specific mutations that create attenuated viruses. The following constitute non-limiting examples of accession nos., each of which are incorporated by reference: human coronavirus 229E (NC002645), SARS TOR2 (AY274119), SARS HKU-39849 (AY278491), SARS CUHK-W1 (AY278554), bovine coronavirus (BCV) (NC003045), avian infectious bronchitis virus (IBV) (NC001451), transmissible gastroenteritis virus (TGEV), (NC002306), mouse hepatitis virus (MHV) (NC001846).

B. Random Mutagenesis

In one embodiment, random mutagenesis may be applied. This will, of course, require an additional step of screening for the desired mutations. Screening will typically be accomplished by nucleic acid hybridization (Southern or Northern blotting), sequencing, or SnP analysis, methods of which are well known to those of skill in the art.

1. Insertional Mutagenesis

Insertional mutagenesis is based on the inactivation of a gene via insertion of a known DNA fragment. Because it involves the insertion of some type of DNA fragment, the mutations generated are generally loss-of-function, rather than gain-of-function mutations. However, there are several examples of insertions generating gain-of-function mutations (Oppenheimer et al. 1991). Insertion mutagenesis has been very successful in bacteria and *Drosophila* (Cooley et al. 1988) and recently has become a powerful tool in corn (Schmidt et al. 1987); *Arabidopsis;* (Marks et al., 1991; Koncz et al. 1990); and *Antirrhinum* (Sommer et al. 1990).

Transposable genetic elements are DNA sequences that can move (transpose) from one place to another in the genome of a cell. The first transposable elements to be recognized were the Activator/Dissociation elements of Zea mays (McClintock, 1957). Since then, they have been identified in a wide range of organisms, both prokaryotic and eukaryotic.

Transposable elements in the genome are characterized by being flanked by direct repeats of a short sequence of DNA that has been duplicated during transposition and is called a target site duplication. Virtually all transposable elements whatever their type, and mechanism of transposition, make such duplications at the site of their insertion. In some cases the number of bases duplicated is constant, in other cases it may vary with each transposition event. Most transposable elements have inverted repeat sequences at their termini. These terminal inverted repeats may be anything from a few bases to a few hundred bases long and in many cases they are known to be necessary for transposition.

Prokaryotic transposable elements have been most studied in E. coli and Gram negative bacteria, but also are present in Gram positive bacteria. They are generally termed insertion sequences if they are less than about 2 kB long, or transposons if they are longer. Bacteriophages such as mu and D108, which replicate by transposition, make up a third type of transposable element. Elements of each type encode at least one polypeptide a transposase, required for their own transposition. Transposons often further include genes coding for function unrelated to transposition, for example, antibiotic resistance genes.

Transposons can be divided into two classes according to their structure. First, compound or composite transposons have copies of an insertion sequence element at each end, usually in an inverted orientation. These transposons require transposases encoded by one of their terminal IS elements. The second class of transposon have terminal repeats of about 30 base pairs and do not contain sequences from IS elements.

Transposition usually is either conservative or replicative, although in some cases it can be both. In replicative transposition, one copy of the transposing element remains at the donor site, and another is inserted at the target site. In conservative transposition, the transposing element is excised from one site and inserted at another.

Eukaryotic elements also can be classified according to their structure and mechanism of transportation. The primary distinction is between elements that transpose via an RNA intermediate, and elements that transpose directly from DNA to DNA.

Elements that transpose via an RNA intermediate often are referred to as retrotransposons, and their most characteristic feature is that they encode polypeptides that are believed to have reverse transcriptionase activity. There are two types of retrotransposon. Some resemble the integrated proviral DNA of a retrovirus in that they have long direct repeat sequences, long terminal repeats (LTRs), at each end. The similarity between these retrotransposons and proviruses extends to their coding capacity. They contain sequences related to the gag and pol genes of a retrovirus, suggesting that they transpose by a mechanism related to a retroviral life cycle. Retrotransposons of the second type have no terminal repeats. They also code for gag- and pol-like polypeptides and transpose by reverse transcription of RNA intermediates, but do so by a mechanism that differs from that or retrovirus-like elements. Transposition by reverse transcription is a replicative process and does not require excision of an element from a donor site.

Transposable elements are an important source of spontaneous mutations, and have influenced the ways in which genes and genomes have evolved. They can inactivate genes by inserting within them, and can cause gross chromosomal rearrangements either directly, through the activity of their transposases, or indirectly, as a result of recombination between copies of an element scattered around the genome. Transposable elements that excise often do so imprecisely and may produce alleles coding for altered gene products if the number of bases added or deleted is a multiple of three.

Transposable elements themselves may evolve in unusual ways. If they were inherited like other DNA sequences, then copies of an element in one species would be more like copies in closely related species than copies in more distant species. This is not always the case, suggesting that transposable elements are occasionally transmitted horizontally from one species to another.

2. Chemical Mutagenesis

Chemical mutagenesis offers certain advantages, such as the ability to find a full range of mutant alleles with degrees of phenotypic severity, and is facile and inexpensive to perform. The majority of chemical carcinogens produce mutations in DNA. Benzo[a]pyrene, N-acetoxy-2-acetyl aminofluorene and aflotoxin B1 cause GC to TA transversions in bacteria and mammalian cells. Benzo[a]pyrene also can produce base substitutions such as AT to TA. N-nitroso compounds produce GC to AT transitions. Alkylation of the 04 position of thymine induced by exposure to n-nitrosoureas results in TA to CG transitions.

A high correlation between mutagenicity and carcinogenity is the underlying assumption behind the Ames test (McCann et al., 1975) which speedily assays for mutants in a bacterial system, together with an added rat liver homogenate, which contains the microsomal cytochrome P450, to provide the metabolic activation of the mutagens where needed.

In vertebrates, several carcinogens have been found to produce mutation in the ras proto-oncogene. N-nitroso-N-methyl urea induces mammary, prostate and other carcinomas in rats with the majority of the tumors showing a G to A transition at the second position in codon 12 of the Ha-ras oncogene. Benzo[a]pyrene-induced skin tumors contain A to T transformation in the second codon of the Ha-ras gene.

3. Radiation Mutagenesis

The integrity of biological molecules is degraded by the ionizing radiation. Adsorption of the incident energy leads to the formation of ions and free radicals, and breakage of some covalent bonds. Susceptibility to radiation damage appears quite variable between molecules, and between different crystalline forms of the same molecule. It depends on the total accumulated dose, and also on the dose rate (as once free radicals are present, the molecular damage they cause depends on their natural diffusion rate and thus upon real time). Damage is reduced and controlled by making the sample as cold as possible.

Ionizing radiation causes DNA damage and cell killing, generally proportional to the dose rate. Ionizing radiation has been postulated to induce multiple biological effects by direct interaction with DNA, or through the formation of free radical species leading to DNA damage (Hall, 1988). These effects include gene mutations, malignant transformation, and cell killing. Although ionizing radiation has been demonstrated to induce expression of certain DNA repair genes in some prokaryotic and lower eukaryotic cells, little is known about the effects of ionizing radiation on the regulation of mammalian gene expression (Borek, 1985). Several studies have described changes in the pattern of protein synthesis observed after irradiation of mammalian cells. For example, ionizing radiation treatment of human malignant melanoma cells is associated with induction of several unidentified proteins (Boothman et al., 1989). Synthesis of cyclin and co-regulated polypeptides is suppressed by ionizing radiation in rat REF52 cells, but not in oncogene-transformed REF52 cell lines (Lambert and Borek, 1988). Other studies have demonstrated that certain growth factors or cytokines may be involved in x-ray-induced DNA damage. In this regard, platelet-derived growth factor is released from endothelial cells after irradiation (Witte et al., 1989).

In the present invention, the term "ionizing radiation" means radiation comprising particles or photons that have sufficient energy or can produce sufficient energy via nuclear interactions to produce ionization (gain or loss of electrons). An exemplary and preferred ionizing radiation is an x-radiation. The amount of ionizing radiation needed in a given cell generally depends upon the nature of that cell. Typically, an effective expression-inducing dose is less than a dose of ionizing radiation that causes cell damage or death directly. Means for determining an effective amount of radiation are well known in the art.

In a certain embodiments, an effective expression inducing amount is from about 2 to about 30 Gray (Gy) administered at a rate of from about 0.5 to about 2 Gy/minute. Even more preferably, an effective expression inducing amount of ionizing radiation is from about 5 to about 15 Gy. In other embodiments, doses of 2-9 Gy are used in single doses. An effective dose of ionizing radiation may be from 10 to 100 Gy, with 15 to 75 Gy being preferred, and 20 to 50 Gy being more preferred.

Any suitable means for delivering radiation to a tissue may be employed in the present invention in addition to external means. For example, radiation may be delivered by first providing a radiolabeled antibody that immunoreacts with an antigen of the tumor, followed by delivering an effective amount of the radiolabeled antibody to the tumor. In addition, radioisotopes may be used to deliver ionizing radiation to a tissue or cell.

4. In vitro Scanning Mutagenesis

Random mutagenesis also may be introduced using error prone PCR (Cadwell and Joyce, 1992). The rate of mutagenesis may be increased by performing PCR in multiple tubes with dilutions of templates.

One particularly useful mutagenesis technique is alanine scanning mutagenesis in which a number of residues are substituted individually with the amino acid alanine so that the effects of losing side-chain interactions can be determined, while minimizing the risk of large-scale perturbations in protein conformation (Cunningham and Wells, 1989).

In recent years, techniques for estimating the equilibrium constant for ligand binding using minuscule amounts of protein have been developed (Blackburn et al., 1991; U.S. Pat. Nos. 5,221,605 and 5,238,808). The ability to perform functional assays with small amounts of material can be exploited to develop highly efficient, in vitro methodologies for the saturation mutagenesis of antibodies. The inventor bypassed cloning steps by combining PCR mutagenesis with coupled in vitro transcription/translation for the high throughput generation of protein mutants. Here, the PCR products are used directly as the template for the in vitro transcription/translation of the mutant single chain antibodies. Because of the high efficiency with which all 19 amino acid substitutions can be generated and analyzed in this way, it is now possible to perform saturation mutagenesis on numerous residues of interest, a process that can be described as in vitro scanning saturation mutagenesis (Burks et al., 1997).

In vitro scanning saturation mutagenesis provides a rapid method for obtaining a large amount of structure-function information including: (I) identification of residues that modulate ligand binding specificity, (ii) a better understanding of ligand binding based on the identification of those amino acids that retain activity and those that abolish activity at a given location, (iii) an evaluation of the overall plasticity of an active site or protein subdomain, (iv) identification of amino acid substitutions that result in increased binding.

5. Random Mutagenesis by Fragmentation and Reassembly

A method for generating libraries of displayed polypeptides is described in U.S. Pat. No. 5,380,721. The method comprises obtaining polynucleotide library members, pooling and fragmenting the polynucleotides, and reforming fragments there from, performing PCR amplification, thereby homologously recombining the fragments to form a shuffled pool of recombined polynucleotides.

C. Site-Directed Mutagenesis

Structure-guided site-specific mutagenesis represents a powerful tool for the dissection and engineering of protein-ligand interactions (Braisted and Wells, 1996), especially in the context of the present invention where specific mutations in cleavage sites are sought. The technique provides for the preparation of sequence variants by introducing one or more discrete nucleotide sequence changes into a selected nucleic acid.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. A primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as *E. coli* polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as *E. coli* cells, and clones are selected that include recombinant vectors bearing the mutated sequence arrangement.

Comprehensive information on the functional significance and information content of a given residue of protein can best be obtained by saturation mutagenesis in which all 19 amino acid substitutions are examined. The shortcoming of this approach is that the logistics of multiresidue saturation mutagenesis are daunting (Warren et al., 1996, Zeng et al., 1996; Barbas et al., 1994; Yelton et al., 1995; Wong et al., 1996; Hilton et al., 1996). Hundreds, and possibly even thousands, of site specific mutants must be studied. However, improved techniques make production and rapid screening of mutants much more straightforward. See also, U.S. Pat. Nos. 5,798,208 and 5,830,650, for a description of "walk-through" mutagenesis.

Other methods of site-directed mutagenesis are disclosed in U.S. Pat. Nos. 5,220,007; 5,284,760; 5,354,670; 5,366,878; 5,389,514; 5,635,377; and 5,789,166.

D. Virus Transformation and Propagation

Targeted recombination has become a powerful tool to introduce mutations into the genome and determine their effects on protein function, virus replication and virus pathogenesis (Koetzner et al., 1992; Masters et al., 1994; Fischer et al., 1997; Lavi et al., 1998; Leparc-Goffart et al., 1998; Phillips et al., 1999; Sanchez et al., 1999; Phillips et al., 2001; de haan et al., 2002; Sarma et al., 2002). However, the available recombination constructs and methodologies have thus far limited the use of targeted recombination, and have not been employed to examine mutations in the replicase gene.

The inventor has previously collaborated in the development of a system for assembly of full-length MHV genome cDNA, generation of genome length RNA, and recovery of virus from transfected cells (Schaad et al., 1990; Yount et al., 2002). In this process, seven contiguous cDNA clones that spanned the 31.5-kb genome of mouse hepatitis virus strain A59 (MHV-A59) were isolated. The ends of the cDNAs were engineered with unique junctions and assembled with only the adjacent cDNA subclones, resulting in an intact MHV-A59 cDNA construct of about 31.5 kb in length. The interconnecting restriction site junctions that are located at the ends of each cDNA are systematically removed during the assembly of the complete full-length cDNA product, allowing reassembly without the introduction of nucleotide changes.

RNA transcripts derived from the full-length MHV-A59 construct were infectious, although transfection frequencies were enhanced 10- to 15-fold in the presence of transcripts encoding the nucleocapsid protein N. Plaque-purified virus derived from the infectious construct replicated efficiently and displayed similar growth kinetics, plaque morphology, and cytopathology in murine cells as did wild-type MHV-A59. Molecularly cloned viruses recognized the MHV receptor (MHVR) for docking and entry, and pretreatment of cells with monoclonal antibodies against MHVR blocked virus entry and replication. Cells infected with molecularly cloned MHV-A59 virus expressed replicase (gene 1) proteins identical to those of laboratory MHV-A59. Importantly, the molecularly cloned viruses contained three marker mutations that had been derived from the engineered component clones.

Using this process, full-length infectious constructs of MHV-A59 and other coronaviruses with genetic modifications of may be created. In fact, the method has the potential to be used to construct viral, microbial, or eukaryotic genomes approaching several million base pairs in length and used to insert restriction sites at any given nucleotide in a microbial genome. A similar system approach was used previously with TGEV, including the insertion of heterologous genes into the TGEV genome (Yount, 2000; Curtis et al., 2002). The inventor described herein the use of this same assembly approach to introduce five different mutations into the MHV p28/p65 cleavage site (CS 1). While the approaches are similar, it was not usually necessary with MHV to introduce mutations and new restriction sites into the wild-type virus genome to direct the assembly cascade. Rather, type IIS restriction endonuclease Esp3I sites can be used to create the unique interconnecting junctions, and yet be subsequently removed from the final assembly product, allowing for the reconstruction of an intact wild-type sequence. This approach avoids the introduction of nucleotide changes that are normally associated with building a full-length cDNA product of a viral genome.

The use of non-palindromic restriction sites also provides other novel recombinant DNA applications. For example, by PCR, it is be possible to insert Esp3I or a related non-palindromic restriction site at any given nucleotide in a viral genome and use the variable domain for simple and rapid site-specific mutagenesis. By orienting the restriction sites as No See'm, the sites are removed during reassembly, leaving only the desired mutation in the final DNA product. The dual properties of strand specificity and a variable end overhang that can be tailored to match any sequence allow for Esp3I sites to be engineered as universal connectors that can be joined with any other 4-nucleotide restriction site overhang (e.g., EcoRI, PstXI, and BamHI). Alternatively, No See'm sites can be used to insert foreign genes into viral, eukaryotic, or microbial genomes or vectors, simultaneously removing all evidence of the restriction sites that were used in the recombinant DNA manipulation.

In order to remove preexisting Esp3I sites that resided within the MHV-A59 genome sequence, silent mutations were created. This helped to distinguish between molecularly cloned and wild-type viruses. In one instance, the Esp3I site at position 4875 was removed because it left a TTAA overhang that would have prevented the directionality of assembly. The other Esp3I sites were removed to minimize the total number of MHV-A59 subdlones used in the assembly cascade. In two instances, silent mutations were inserted into the Esp3I overhang to maximize sequence specificity and directionality at a particular junction, but this could be circumvented by choosing slightly different junction sites. Clearly, each virus sequence will need to be evaluated for the need for similar changes.

cDNA cassettes can be ligated systematically as previously described for TGEV, or simultaneously as described herein. Although numerous incomplete assembly intermediates occur were evident, the inventor has found that simultaneous ligation of seven cDNAs will result in full-length cDNA, thereby simplifying the complexity of the assembly strategy. There is no evidence to indicate that this approach might introduce spurious mutations or genome rearrangements from aberrant assembly cascades. And while it is possible that such variants might arise following RNA transfection (as a consequence of high-frequency MHV RNA recombination between incomplete and genome-length transcripts), it is highly likely that such variants would be replication impaired and rapidly outcompeted by wild-type virus. A second limitation is that the yield of full-length cDNA product is reduced, resulting in less robust transfection efficiencies than those of the more traditional systematic assembly method. This downside is more than compensated by the reduced complexity in many cases.

V. Vaccines

A. Formulations and Administration

The present invention provides for Nidovirus vaccine formulations. Such compositions will generally be dissolved or dispersed in a pharmaceutically acceptable carrier or aqueous medium. There are numerous examples of vaccine formulations in the literature, and one of skill in the art will be capable of formulating such vaccines.

The phrases "pharmaceutically acceptable" or "pharmacologically acceptable" refer to molecular entities and compositions that do not produce an adverse, allergic, or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art.

The vaccines of the present invention can be formulated for parenteral administration, e.g., formulated for injection via the intravenous, intramuscular, subcutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and, the preparations can also be emulsified. The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques. In certain cases, the therapeutic formulations of the invention also may be prepared in forms suitable for oral or intranasal administration.

An effective amount of the vaccine is determined based on the intended goal. The term "unit dose" or "dosage" refers to physically discrete units suitable for use in a subject, each unit containing a predetermined-quantity of the composition calculated to produce the desired responses, discussed above, in association with its administration, i.e., the appropriate route and treatment regimen. Precise amounts of the vaccine composition also depend on the judgment of the practitioner and are peculiar to each individual. Factors affecting dose include physical and clinical state of the patient, the route of administration, the intended goal of treatment (alleviation of symptoms versus cure) and the potency, stability, and toxicity of the particular substance.

The following is a listing of references describing various live vaccines, the relevant contents of which (formulations and administration) are hereby incorporated by reference:

U.S. Pat. Nos. 6,479,056 ; 6,444,445; 6,306,400; 6,296,854; 6,231,871; 6,217,882; 6,159,477; 6,153,199; 6,136,325; 6,077,516; 6,051,237; 6,045,803; 6,039,958; 6,039,941; 6,033,670; 5,993,822; 5,980,906; 5,958,423; 5,948,411; 5,871,742; 5,869,036; 5,792,452; 5,733,555; 5,733,554; 5,651,972; 5,632,989; 5,626,850; 5,580,557; 5,436,001; 5,310,668; 5,149,531; 5,068,104; 5,037,650; 5,024,836; 5,006,335; 4,985,244; 4,980,162; 4,808,404; 4,770,875; 4,762,711; 4,752,474; 4,673,572; 4,645,665; 4,624,850; 4,590,072; 4,555,401; 4,554,158; 4,472,378; 4,456,588; 4,324,861; 4,311,797; 4,235,876; 4,004,974

B. Additional Agents

In addition to the inactive agents discussed above, the vaccine may comprise, or may be given in conjunction with, a supplemental agent. One example is an immunostimulant.

VI. EXAMPLES

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Viruses and cells. Mouse hepatitis virus lab strain RA59 was the wildtype control in all experiments. Delayed brain tumor (DBT) cells and baby hamster kidney cells expressing the MHV receptor (BHK-MHVR) were grown in Dulbecco's modified Eagle medium (DMEM) containing 10% fetal calf serum (FCS). The BHK-MHVR cells were grown under G418 selection (0.8 mg/ml).

Sequencing MHV cDNA fragments. The infectious clone MHV cDNA fragments (A-G) were sequenced with a set of primers designed from the MHV genome (NCBI accession: NC001846). Sequencing primers were created every 600 bp, beginning with the 5' end, of both the sense and antisense strands. These primers generated overlapping sequences covering the cDNA clones at least twice, and up to four times in certain regions. M13 forward and reverse primers were also used to sequence the insert-vector junction of the pCR-XL-Topo (Invitrogen) or pSMART-LCAmp (Lucigen) parent vectors. The sequencing was performed with an ABIPrism automated sequencer. The sequences were aligned and compared with MHV sequences from the NCBI database: NC001846, AF029248, AF201929, AF207902, AF208066, AF208067, M18379, M55148, X00509, X51939, X57302, and X73559.

Site-directed mutagenesis of fragment F. Site-directed mutations were made in the fragment F plasmid, which consists of genomic nucleotides (nt) 15755 to 22740, at nt 19400 and 22051 using PCR. A 5' BstBI and 3' AflII site or a 5' AflII and 3' SpeI site were used to clone the PCR product with the C19400T correction or C22051T correction, respectively, into the pCR-XL-Topo-F. The resultant F plasmids are (pCR-XL-Topo-F 19400T, 22051C), (pCR-XL-Topo-F 19400C, 2205 1T), and (pCR-XL-Topo-F 19400T, 2205 1T).

Virus assembly. The reverse genetics system for MHV-A59 was used to create viruses with the engineered mutations. Briefly, plasmids A through G containing cDNA cassettes of the MHV genome were digested. The digested fragments were gel purified and ligated together, following which full-length transcripts were generated in vitro using the mMessage mMachine T7 Transcription Kit (Ambion), following the manufacturer's protocol with modifications. Breifly, a 50 μL reaction was supplemented with 7.5 μL of 30 mM GTP and the transcription reaction was performed at 40.5° C. for 25 minutes, 37.5° C. for 50 minutes, and 40.5° C. for 25 minutes. The icMHV transcripts were then combined with N transcripts generated in vitro and 600 μL of BHK-MHVR cells in PBS ($10^7$ cells/ml) in a 4 mm gap cuvette and three electrical pulses of 850 V at 25 μF were delivered to the mixture with a Bio-Rad Gene Pulser Xcell electroporator. Transfected cells were seeded over a layer of $10^6$ uninfected DBT cells in a 75 cm² flask and incubated at 37° C. for 30 hours. Virus viability was determined by synctia formation, and progeny virus was passaged and purified by plaque assay.

RT-PCR and sequencing of viral RNA. Plaque isolated virus was used to infect DBT cells in 25 cm² flasks (~$3\times10^6$ cells) at a high MOI. With ~80% of the monolayer involved in synctitia, the cells were lysed with TRIzol reagent (Invitrogen) and total RNA was isolated according to the manufacturer's protocol. An antisense primer complimentary to nt 22126 through 22144 of the MHV genome was used to generate viral cDNA from the total RNA using reverse transcription. The RT product was amplified by PCR with the same antisense primer and a sense primer complimentary to nt 19321 through nt 19338. This PCR product was then sequenced using an ABIPrism automated sequencer over nt 19400 and nt 22051 to confirm the mutations present for each virus.

Determination of viral titer from brain of infected mice. Mice were infected with each virus. Five mice per virus were sacrificed 5 d p.i. and 5 mice per virus 7 d p.i. The brains were weighed and placed in 2 ml saline, homogenized, and stored at −70° C. The number of infectious virus in the brain was titered on DBT cells. Plaque isolates of each virus were harvested and sequenced using RT-PCR as described in the previous section. One plaque isolate from two different mice per virus was sequenced over nt 19400 and nt 22051.

Growth experiments. Duplicate DBT cells ($10^7$) in 75 cm² flasks were infected at an MOI of 5 PFU/cell with plaque isolates from the first passage of each virus. The cells were rocked for 30 minutes and then washed three times with PBS (10 minutes per wash). Media was added (10 mL) and the cells were incubated at 37° C. Samples of media (0.5 mL) were collected at 1 h, 4 h, 8 h, 12 h, 16 h, and 25 h p.i., and viral titers were determined by plaque assay.

Example 2

Results icMHV virulence attenuated in mice. The inventor's lab has previously shown that a wild-type MHV infectious clone virus (icMHV) demonstrated a wild-type phenotype in growth, protein processing, and RNA synthesis assays in DBT cell culture. To determine whether icMHV is virulent in mice, $10^5$ pfu of both wild-type A59 and icMHV were injected into mice. 100% of mice inoculated with wild-type lab strain A59 eventually died. Surprisingly, none of the mice inoculated with icMHV died or became ill, suggesting that icMHV was attenuated. It was hypothesized that an unaccounted mutation in the icMHV was responsible for attenuating the virus.

Identification of possible virulence attenuating mutations in icMHV. To identify all possible mutations in the icMHV that could cause this lack of virulence, the inventor sequenced the entire cDNA genome of the infectious clone. The cDNA constructs (A-G) of the MHV infectious clone were sequenced bi-directionally using overlapping sets of primers. This strategy generated sequences covering the genome at least twice, and up to four times, confirming the sequence of the infectious clone. The sequences were initially compared with the published MHV-A59 genome sequence of the C12 mutant virus,.(NCBI accession #NC001846). Compared to this sequence, the inventor identified 17 silent and 5 coding differences in clones A-F, and an additional 11 silent and 6 coding differences in the G clone. The G clone was derived from the pMH54 plasmid, and the coding differences found within the G clone have previously been reported. Furthermore, studies have shown viruses generated by homologous recombination using a pMH54 derivative to be virulent. Therefore our analysis focused on the five coding differences residing in the first ~22.7 kb of the genome: two in fragment B (nt T5304C and A6796T) and three in fragment F (nt T17533G, T19400C, and T22051C). The first two mutations (nt T5304C and A6796T) were previously reported for the infectious clone. The first three coding differences between the icMHV and the C12 mutant virus at nt 5304, 6796, and 17533 coincided with the positions of nucleotide mutations reported for the C12 mutant virus. Upon comparison to other MHV sequences available for both strains A59 and JHM, the inventor found that the nucleotides at the first three positions (nt C5304, T6796, and G17533) were identical to these other sequences. The final two mutations, T19400C and T22051C, were not described in any of the available MHV-A59 and MHV-JHM sequences. The first of these mutations coded a tyr6398 his amino acid change in the Orf1ab polyprotein. The latter mutation was a leu$^{106}$pro amino acid change in the Orf2a protein. Among group 2 coronaviruses that possess the Orf2a protein, the leucine residue is conserved. The former tyr$^{6398}$his mutation lies in MHV nsp14 (p59) and the tyrosine is conserved for all coronaviruses. Thus, sequencing of the icMHV cDNA identified two novel candidate mutations at conserved residues that were possibly responsible for attenuating the icMHV virus.

Correction of candidate attenuating mutations in icMHV. To determine whether either, both, or neither of the identified mutations was the cause of the attenuating phenotype in icMHV, the inventor corrected each mutation individually and simultaneously. The nt T19400C and T22051C mutations are both found in the F fragment of the MHV infectious clone. Site-directed PCR mutagenesis was used to individually correct the two mutations, changing them back to wild-type sequence at that nucleotide. Hence, the inventor corrected the amino acid at 6398 in Orf1ab from a histidine to the wild-type tyrosine and the amino acid at 106 in Orf2a protein from a proline to the wild-type leucine. Using the reverse genetics system, the inventor assembled viruses with each possible combination of corrected and uncorrected residues. VUSS 0 was made with the original, uncorrected histidine and proline residues. VUSS 1 corrected the Orf1ab mutation, with the combination of tyrosine at position 6398 and proline at position 106. VUSS 2 corrected the Orf2a protein, with a histidine at position 6398 and leucine at position 106. VUSS 3 corrected both sites with a tyrosine and leucine combination. The viruses were sequenced following three successive passages in cell culture, confirming the mutations were present and maintained (data not shown).

Uncorrected and corrected viruses exhibit wild-type growth in DBT cells. The assembled viruses grew in DBT cells to titers approximately the same as lab strain MHV-A59 virus. There was no observed difference in plaque morphology. Single-cycle growth curve experiments performed at an MOI of 5 PFU/cell demonstrated that there was no distinguishable difference in the growth kinetics of these viruses in culture. Peak titers >$10^6$ PFU/ml for each virus were achieved at 12 h p.i. Thus, there was no difference between lab strain MHV-A59 and the corrected and uncorrected viruses, in agreement with our previous results with the original icMHV.

Both Orf1ab and Orf2a mutations attenuate MHV-A59 in mice. The virulence of the four infectious clone viruses were examined alongside lab strain MHV-A59 in mice. The inventors calculated $LD_{50}$ values for each virus. Wild-type A59 and VUSS 3 both had an $\log_{10} LD_{50}$ of 3.8. VUSS 0 and VUSS 2 both had an $\log_{10} LD_{50} > 5.3$. This data indicated that VUSS 0, with both uncorrected histidine and proline mutations, and VUSS 2, with just the histidine mutation in Orf1ab uncorrected, were completely attenuated in mice. Correcting both mutations to the conserved tyrosine and leucine, as in VUSS 3, restores wild-type virulence. VUSS 1, with just the uncorrected proline mutation in Orf2a, appeared to be partially attenuated. Thus, these results demonstrated that the single tyrosine to histidine mutation in the p59 protein of the Orf1ab polyprotein completely eliminated the virulence of MHV-A59 in mice.

Attenuated MHV viruses have reduced replication in mice at day five following IC inoculation. To determine whether the completely attenuated viruses were replicating in vivo, mice were inoculated intra-cranially with VUSS 0, VUSS 2, VUSS 3, and lab strain MHV-A59. Five mice per virus were sacrificed on day 5 and again on day 7 and their organs were collected. Supernatant from the homogenized brain of each mouse was used in plaque assays to determine virus titer at each day. At day five p.i., the virulent viruses wtA59 and VUSS 3 had viral titers of approximately $10^4$ PFU/gram brain tissue, while the attenuated viruses VUSS 0 and VUSS 2 had titers of approximately $10^2$ PFU/gram brain tissue. At 7 d p.i., each of the viruses had been cleared from the mice brains. These results suggest that the avirulent viruses VUSS 0 and VUSS 2 were able to replicate in the brains of the mice, although the avirulent viruses had reduced replication compared to the virulent viruses.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention as defined by the appended claims.

VII. REFERENCES

The following references, to the extent that they provide exemplary procedural or other details supplementary to those set forth herein, are specifically incorporated herein by reference:

U.S. Pat. No. 4,004,974
U.S. Pat. No. 4,235,876
U.S. Pat. No. 4,311,797
U.S. Pat. No. 4,324,861
U.S. Pat. No. 4,456,588
U.S. Pat. No. 4,472,378
U.S. Pat. No. 4,554,158
U.S. Pat. No. 4,555,401
U.S. Pat. No. 4,590,072
U.S. Pat. No. 4,624,850
U.S. Pat. No. 4,645,665
U.S. Pat. No. 4,673,572
U.S. Pat. No. 4,752,474
U.S. Pat. No. 4,762,711
U.S. Pat. No. 4,770,875
U.S. Pat. No. 4,808,404
U.S. Pat. No. 4,980,162
U.S. Pat. No. 4,985,244
U.S. Pat. No. 5,006,335
U.S. Pat. No. 5,024,836
U.S. Pat. No. 5,037,650
U.S. Pat. No. 5,068,104
U.S. Pat. No. 5,149,531
U.S. Pat. No. 5,220,007
U.S. Pat. No. 5,221,605
U.S. Pat. No. 5,238,808
U.S. Pat. No. 5,284,760
U.S. Pat. No. 5,310,668
U.S. Pat. No. 5,354,670
U.S. Pat. No. 5,366,878
U.S. Pat. No. 5,380,721
U.S. Pat. No. 5,389,514
U.S. Pat. No. 5,436,001
U.S. Pat. No. 5,580,557
U.S. Pat. No. 5,626,850
U.S. Pat. No. 5,632,989
U.S. Pat. No. 5,635,377
U.S. Pat. No. 5,651,972
U.S. Pat. No. 5,733,554
U.S. Pat. No. 5,733,555
U.S. Pat. No. 5,789,166
U.S. Pat. No. 5,792,452
U.S. Pat. No. 5,798,208
U.S. Pat. No. 5,830,650
U.S. Pat. No. 5,869,036
U.S. Pat. No. 5,871,742
U.S. Pat. No. 5,948,411
U.S. Pat. No. 5,958,423
U.S. Pat. No. 5,980,906
U.S. Pat. No. 5,993,822
U.S. Pat. No. 6,033,670
U.S. Pat. No. 6,039,941
U.S. Pat. No. 6,039,958
U.S. Pat. No. 6,045,803
U.S. Pat. No. 6,051,237
U.S. Pat. No. 6,077,516
U.S. Pat. No. 6,136,325
U.S. Pat. No. 6,153,199
U.S. Pat. No. 6,159,477
U.S. Pat. No. 6,217,882
U.S. Pat. No. 6,231,871

U.S. Pat. No. 6,296,854
U.S. Pat. No. 6,306,400
U.S. Pat. No. 6,444,445
U.S. Pat. No. 6,479,056
Baker et al., *J Virol.*, 67:6056-6063, 1993.
Barbas et al., *Proc. Natl. Acad. Sci. USA*, 91(9):3809-3813, 1994.
Blackburn et al., *J. Lipid. Res.*, 32(12):1911-1918, 1991.
Bonilla et al., *J. Virol.*, 71:900-909, 1997.
Bonilla et al., *Virology*, 209:489-497, 1995.
Boothman et al., *Cancer Res.*, 49(11):2871-2878, 1989.
Borek, *Carcinog. Compr. Surv.*, 10:303-316, 1985.
Boursnell et al., *J. Gen. Virol.*, 68:57-77, 1987.
Braisted and Wells, *Proc. Natl. Acad. Sci. USA*, 93(12):5688-5692, 1996.
Burks et al., *Proc. Natl. Acad. Sci. USA*, 94(2):412-417, 1997.
Caldwell and Joyce, *PCR Methods Appl.*, 2(1):28-33, 1992.
Chouljenko et al., *J. Gen. Virol.*, 82:2927-2933, 2001.
Cooley et al., *Science*, 239(4844):1121-1128, 1988.
Cunningham and Wells, *Science*, 244(4908):1081-1085, 1989.
Curtis et al., *J. Virol.*, 76:1422-1434, 2002.
de Haan et al., *Virology*, 296:177-189, 2002.
Dong and Baker, *Virology*, 204:541-549, 1994.
Eleouet et al., *Virology*, 206:817-822, 1995.
Fischer et al., *J. Virol.*, 71:5148-5146, 1997.
Hall, *Genetics*, 120(4):887-897, 1988.
Herold et al., *J. Biol. Chem.*, 274:14918-14925, 1999.
Herold et al., *Virology*, 195:680-691, 1993.
Hilton et al., *J. Biol. Chem.*, 271(9):4699-4708, 1996.
Hughes et al., *J. Virol.*, 69:809-813, 1995.
Kanjanahaluethai and Baker, *J. Virol.*, 74:7911-7921, 2000.
Kanjanahaluethai et al., *Adv. Exp. Med. Biol.*, 494:267-273, 2001.
Koetzner et al., *J. Virol.*, 66:1841-1848, 1992.
Koncz et al., *EMBO J.*, 9(5):1337-1346, 1990.
Lambert and Borek, *J. Natl. Cancer Inst.*, 80(18):1492-1497, 1988.
Lavi et al., *Adv. Exp. Med. Biol.*, 440:543-547, 1998.
Lee et al., *Virology*, 180:567-582, 1991.
Leparc-Goffart et al., *J. Virol.*, 72:9628-9636, 1998.
Marks et al., *Symp. Soc. Exp. Biol.*, 45:77-87, 1991.
Masters et al., *J. Virol.*, 68:328-337, 1994.
McCann et al., *Proc. Natl. Acad. Sci. USA*, 72(3):979-983, 1975.
McClintok et al, *Am. J. Physiol.*, 189(3):463-469, 1957.
Oppenheimer et al., *Cell*, 67(3):483-493, 1991.
Phillips et al., *J. Neurovirol.*, 7:421-431, 2001.
Phillips et al., *J. Virol.*, 73:7752-7760, 1999.
Sanchez et al., J. Virol., 73:7607-7618, 1999.
Sarma et al., *J. Neurovirol.*, 8:381-391, 2002.
Schaad et al., *Virology*, 177:634-645, 1990.
Schiller et al., *Virology*, 242:288-302, 1998.
Schmidt et al., *Science*, 238(4829):960-963, 1987.
Sommer et al. *EMBO J.*, 9(3):605-613, 1990.
Tijms et al., *Proc. Natl. Acad. Sci. USA*, 98:1889-1894, 2001.
Warren et al., *Biochemistry*, 35(27):8855-8862, 1996.
Witte et al., *Cancer Res.*, 49(18):5066-5072, 1989.
Wong et al., *J Bacteriol.*, 178(8):2334-2342, 1996.
Yelton et al., *J. Immunol.*, 155(4):1994-2004, 1995.
Yoo and Pei, *Adv. Exp. Med. Biol.*, 494:73-76, 2001.
Yount et al., *J. Virol.*, 76:11065-11078, 2002.
Yount, *J. Virol.*, 74:10600-10611, 2000.
Zeng et al., *Biochemistry*, 35(40):13157-13164, 1996.
Ziebuhr et al., *J. Biol. Chem.*, 276:33220-33232, 2001.

---

What is claimed is:

1. A live, attenuated virus groups 2 coronavirus wherein said virus is characterized as comprising a genome encoding (i) an ExoN comprising a substitution at tyrosine$^{6398}$ of MHV-A59, or an analogous position thereof, an (ii) an Orf2a polypeptide comprising a substitution at leu$^{106}$ of MHV-A59, or an analogous position thereof.

2. The virus of claim 1, wherein said coronavirus is bovine coronavirus, human coronavirus OC43, murine hepatitis virus, porcine hemagglutinating encephalomyelitis virus, rat coronavirus, or severe acute respiratory syndrome virus.

3. The virus of claim 1, wherein said virus further comprises a mutation in least one polyprotein proteinase cleavage site that exhibits reduced as compared to wild-type or no cleavage.

4. The virus of claim 3, wherein the cleavage site is a C1-C 14 cleavage site.

5. The virus of claim 3, wherein the cleavage site is a MHV p28-p65 or p65-p210 cleavage site or analogous position thereof.

6. The virus of claim 3, wherein the cleavage site comprises an amino acid deletion, an amino acid insertion or an amino acid substitution.

7. The virus of claim 1, wherein said tyrosine$^{6398}$ substitution is a non-conservative substitution.

8. The virus of claim 1, wherein said tyrosine$^{6398}$ substitution is a histidine.

9. The virus of claim 1, wherein said leu$^{106}$ substitution is a non-conservative substitution.

10. The virus of claim 1, wherein said leu$^{106}$ substitution is a proline.

11. The virus of claim 1, wherein said virus genome further encodes a mutation in one or more of nsp1, nsp2, nsp3, nsp4, nsp5, nsp6, nsp7, nsp8, nsp9, nsp10, nsp11, nsp12, nsp13, nsp15 or nsp16 coding region.

12. A method of inducing an anti-viral immune response in a host comprising administering to said host a live, attenuated group 2 coronavirus wherein said virus is characterized as comprising a genome encoding (i) an ExoN comprising a substitution at tyrosine$^{6398}$ of MHV-A59, or an analogous position thereof, and (ii) an Orf2a polypeptide comprising a substitution at leu$^{106}$ of MHV-A59, or an analogous position thereof.

13. The method of claim 12, wherein the coronavirus is bovine coronavirus, human coronavirus OC43, murine hepatitis virus, porcine hemagglutinating encephalomyelitis virus, rat coronavirus, severe acute respiratory syndrome virus, human coronavirus NL63 or human coronavirus NL.

14. The method of claim 12, wherein said virus further comprises a mutation in least one polyprotein proteinase cleavage site that exhibits wild-type or reduced cleavage as opposed no cleavage.

15. The method of claim 14, wherein the cleavage site is a C1-C14 cleavage site.

16. The method of claim 14, wherein the cleavage site is a MHV p28-p65 or p65-p210 cleavage site or analogous position thereof.

17. The method of claim 14, wherein the cleavage site contains an amino acid deletion, an amino acid insertion or an amino acid substitution.

18. The method of claim 12, wherein said tyrosine$^{6398}$ substitution is a non-conservative substitution.

19. The method of claim 12, wherein said tyrosine$^{6398}$ substitution is a histidine.

20. The method of claim 12, wherein said leu106 substitution is a non-conservative substitution.

21. The method of claim 12, wherein said leu$^{106}$ substitution is a proline.

22. The method of claim 12, wherein said virus genome further encodes a mutation in one or more of nsp1, nsp2, nsp3, nsp4, nsp5, nsp6, nsp7, nsp8, nsp9, nsp10, nsp11, nsp12, nsp13, nsp15 or nsp16 coding region.

23. The method of claim 12, wherein said vaccine is administered intravenously or subcutaneously.

24. The method of claim 12, further comprising administering an immunostimulant.

25. The method of claim 12, wherein said host is a dog, a cow, a pig, a mouse, a rat, or a human.

26. A coronavirus genome, said genome encoding an ExoN polypeptide comprising a substitution at tyrosine6398 of MHV-A59, or an analogous position thereof.

27. An isolated and purified nucleic acid segment encoding coronavirus ExoN polypeptide comprising comprising a substitution at tyrosine$^{6398}$ of MHV-A59, or an analogous position thereof.

28. A composition comprising (a) a live, attentuated group 2 coronavirus, said virus characterized as comprising a genome encoding (i) an ExoN polypeptide comprising comprising a substitution at tyrosine$^{6398}$ of MHV-A59, or an analogous position thereof, and (ii) an Orf2a polypeptide comprising a substitution at leu$^{106}$ of MHV-A59, or an analogous position thereof, and (b) a pharmaceutically acceptable diluent.

29. The composition of claim 28, wherein said composition is formulated as a unit dose of $10^6$ to $10^{14}$ infectious particles.

30. The composition of claim 28, wherein said unit dose is provided in a 100 ml aliquot.

31. The composition of claim 28, further comprising a preservative.

32. The composition of claim 28, wherein said composition is lyophilized.

* * * * *

UNITED STATES PATENT AND TRADEMARK OFFICE
CERTIFICATE OF CORRECTION

PATENT NO.         : 7,452,542 B2                                                Page 1 of 1
APPLICATION NO. : 11/135603
DATED              : November 18, 2008
INVENTOR(S)        : Mark Denison It is certified that error appears in the above-identified patent and that said Letters Patent is hereby corrected as shown below:

In claim 1, column 53, line 44, delete "groups" and insert --group-- therefor.

In claim 1, column 53, line 44, insert comma after "coronavirus".

In claim 1, column 53, line 47, delete "an (ii)" and insert --and (ii)-- therefor.

In claim 12, column 54, lines 55-56, delete "attentuated" and insert --attenuated-- therefor.

In claim 20, column 55, line 17, delete "leu106" and insert --leu$^{106}$-- therefor.

In claim 26, column 56, line 4, delete "tyrosine6398" and insert --tyrosine$^{6398}$-- therefor.

In claim 27, column 56, line 7, delete "comprising comprising" and insert --comprising-- therefor.

In claim 28, column 56, line 10, delete "attentuated" and insert --attenuated-- therefor.

In claim 28, column 56, lines 12-13, delete "comprising comprising" and insert --comprising-- therefor.

Signed and Sealed this

Tenth Day of February, 2009

JOHN DOLL
*Acting Director of the United States Patent and Trademark Office*